(12) United States Patent
Parsonage et al.

(10) Patent No.: US 10,010,311 B2
(45) Date of Patent: Jul. 3, 2018

(54) SEALANT MIXING CONTAINERS FOR EXTRA VASCULAR BIOADHESIVE DELIVERY SYSTEMS AND METHODS

(71) Applicant: ST. JUDE MEDICAL PUERTO RICO LLC, Caguas, PR (US)

(72) Inventors: Edward E. Parsonage, St. Paul, MN (US); Zachary J. Tegels, Minneapolis, MN (US); Martha Escobar, Jordan, MN (US); Russell D. Terwey, St. Michael, MN (US); Troy T. White, Maple Grove, MN (US); Timothy M. McGlinch, St. Paul, MN (US); Bernhard Kaeferlein, Champlin, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1221 days.

(21) Appl. No.: 13/770,586

(22) Filed: Feb. 19, 2013

(65) Prior Publication Data

US 2013/0269299 A1    Oct. 17, 2013

Related U.S. Application Data

(60) Provisional application No. 61/622,865, filed on Apr. 11, 2012.

(51) Int. Cl.
*A61B 17/03*    (2006.01)
*A61B 17/00*    (2006.01)
(Continued)

(52) U.S. Cl.
CPC .... *A61B 17/00491* (2013.01); *A61B 17/0057* (2013.01); *A61B 2017/0065* (2013.01);
(Continued)

(58) Field of Classification Search
CPC ........ A61M 5/19; A61M 5/284; A61M 5/285; A61M 5/286; A61B 17/00491;
(Continued)

(56) References Cited

U.S. PATENT DOCUMENTS 4,676,256 A * 6/1987 Golden ................ A61B 5/1427
                                                600/575
4,735,616 A * 4/1988 Eibl ................. A61B 17/00491
                                                604/191

(Continued)

*Primary Examiner* — Aarti B Berdichevsky
(74) *Attorney, Agent, or Firm* — Dorsey & Whitney LLP

(57) ABSTRACT

A closure device operable to seal a vessel puncture and including a delivery member and a sealant material applicator. The delivery member is insertable through a tissue tract to the vessel puncture. The sealant material applicator is configured to supply a volume of sealant material to the delivery member and includes a housing, a plunger assembly, and at least one container. The housing includes at least first and second chambers, wherein the first chamber carries a first sealant component and the second chamber carries a second sealant component. The container is insertable into the first or second chamber and carries a third sealant component of the sealant material. The sealant material applicator creates flow communication between the container and at least one of the first and second chambers to mix the third sealant component with the first and second sealant components.

9 Claims, 18 Drawing Sheets

(51) Int. Cl.
 *A61B 17/22* (2006.01)
 *A61M 25/00* (2006.01)
(52) U.S. Cl.
 CPC ............... *A61B 2017/00495* (2013.01); *A61B 2017/22067* (2013.01); *A61M 25/0032* (2013.01)
(58) Field of Classification Search
 CPC ...... A61B 17/0057; A61B 2017/00495; A61B 2017/0065
 See application file for complete search history.

(56) References Cited

U.S. PATENT DOCUMENTS

| | | | |
|---|---|---|---|
| 5,814,022 A * | 9/1998 | Antanavich | A61B 17/00491 604/181 |
| 6,045,569 A | 4/2000 | Kensey et al. | |
| 6,090,130 A | 7/2000 | Nash et al. | |
| 6,471,670 B1 * | 10/2002 | Enrenfels | A61B 17/00491 604/191 |
| 7,575,131 B2 * | 8/2009 | Feinberg | A61B 17/00491 222/1 |
| 8,333,787 B2 | 12/2012 | Pipenhagen et al. | |
| 8,506,592 B2 | 8/2013 | Killion et al. | |
| 9,131,930 B2 * | 9/2015 | Greter | A61B 17/00491 |
| 9,398,913 B2 * | 7/2016 | Tegels | A61B 17/08 |
| 2001/0016709 A1 * | 8/2001 | Tovey | A61B 17/00491 604/153 |
| 2004/0068266 A1 * | 4/2004 | Delmotte | A61B 17/8816 606/92 |
| 2005/0027240 A1 * | 2/2005 | Fehr | A61C 5/064 604/82 |
| 2007/0012724 A1 * | 1/2007 | Feinberg | A61B 17/00491 222/137 |
| 2008/0060970 A1 * | 3/2008 | Wheeler | A61B 17/00491 206/570 |
| 2008/0103564 A1 * | 5/2008 | Burkinshaw | A61B 17/00491 607/96 |
| 2011/0166595 A1 | 7/2011 | Vidlund et al. | |
| 2011/0282383 A1 | 11/2011 | Vidlund et al. | |
| 2013/0006299 A1 | 1/2013 | Pipenhagen et al. | |
| 2013/0190808 A1 | 7/2013 | Tegels et al. | |
| 2013/0190812 A1 | 7/2013 | Vidlund | |
| 2013/0190813 A1 | 7/2013 | Tegels et al. | |
| 2014/0058442 A1 * | 2/2014 | Tegels | A61B 17/08 606/214 |
| 2014/0135831 A1 * | 5/2014 | White | A61B 17/00491 606/214 |

* cited by examiner

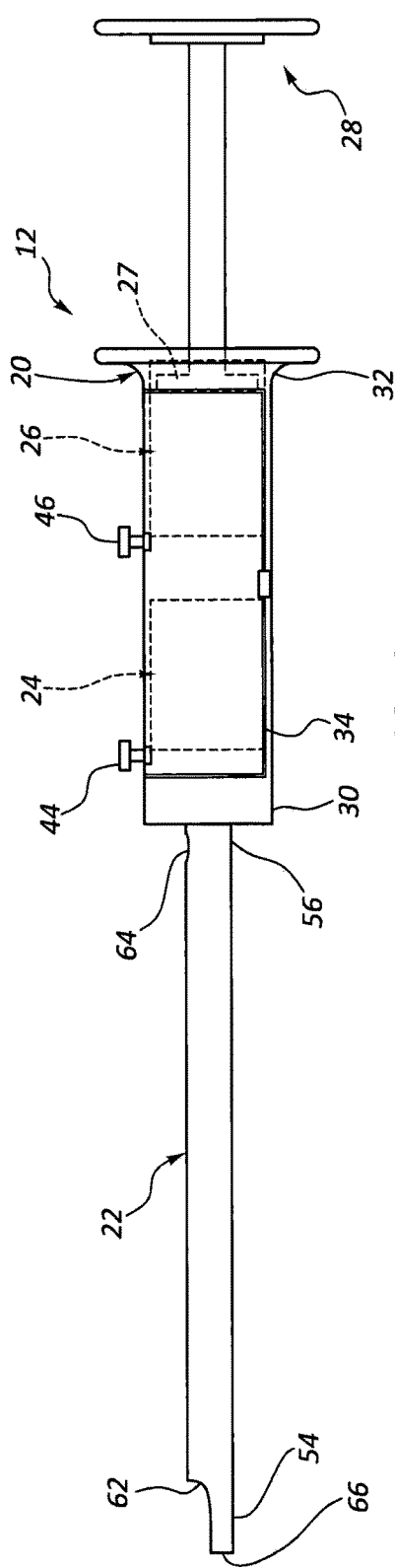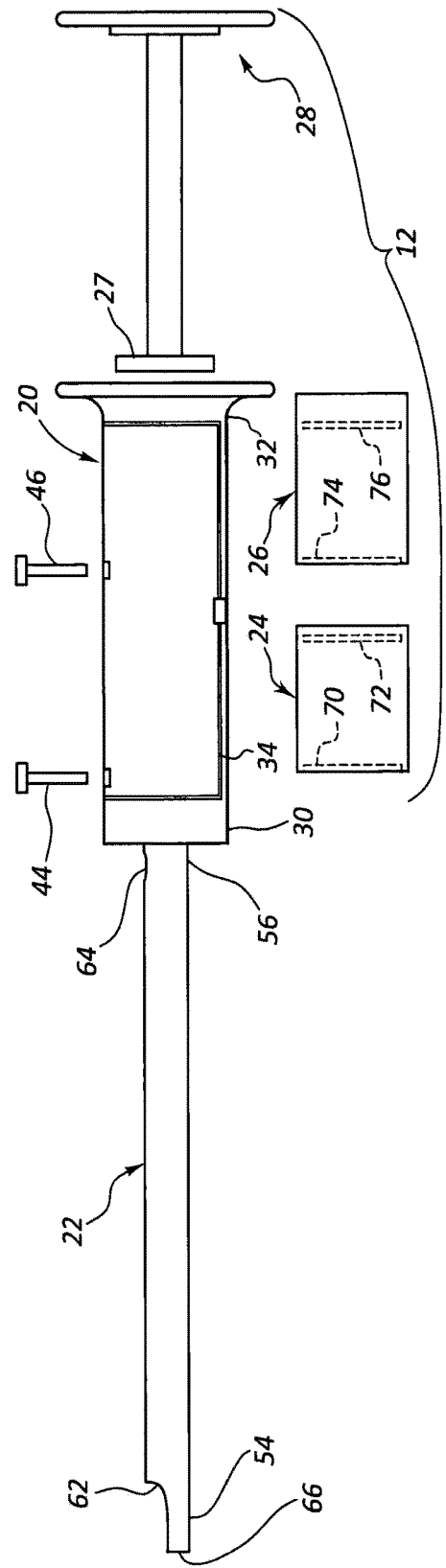
FIG. 1
FIG. 2

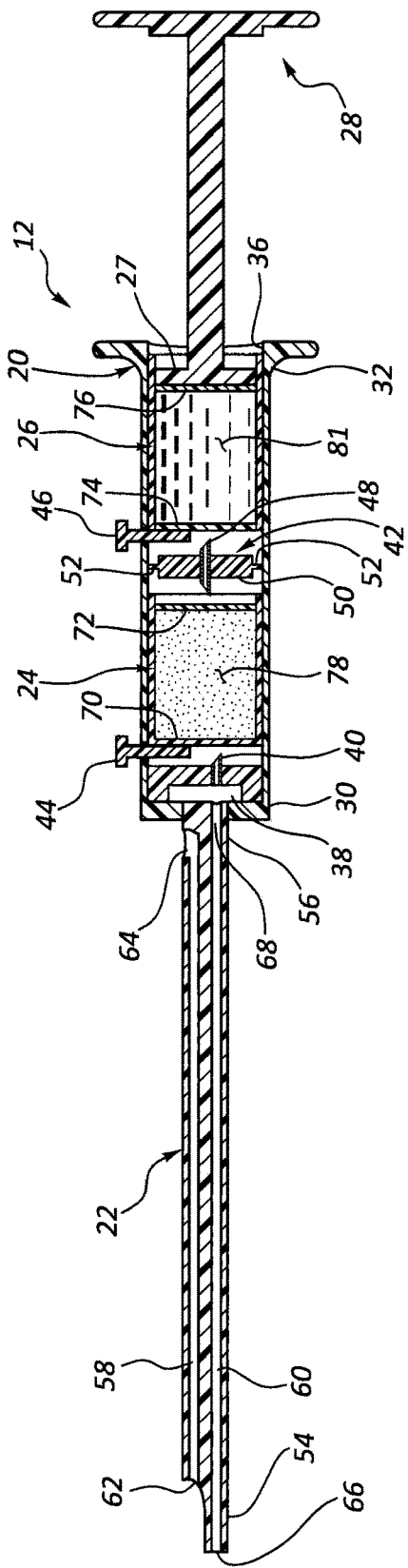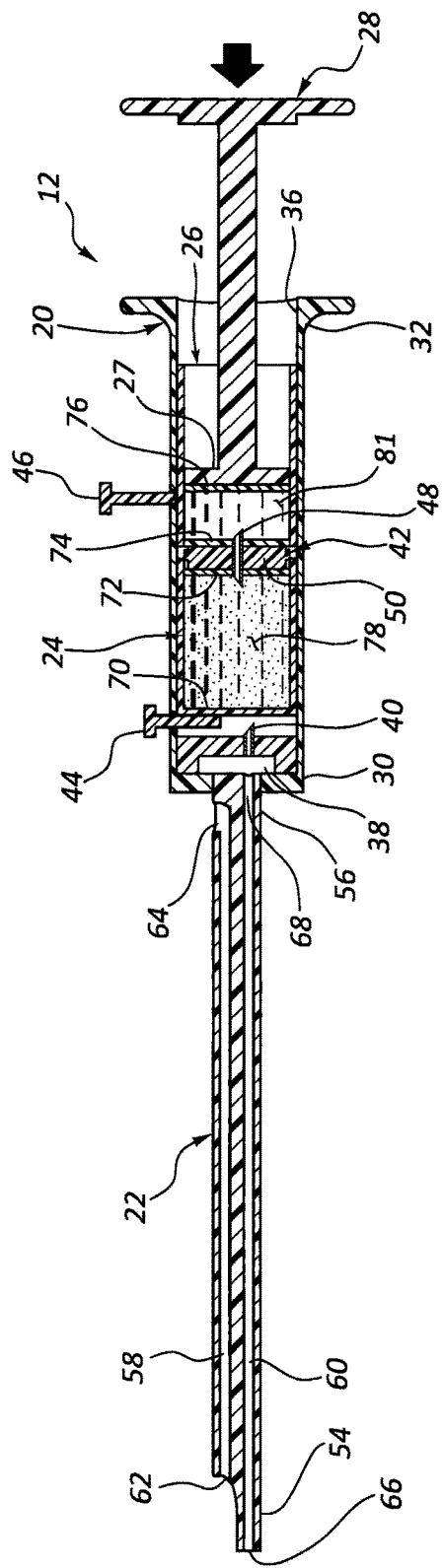
FIG. 3
FIG. 4

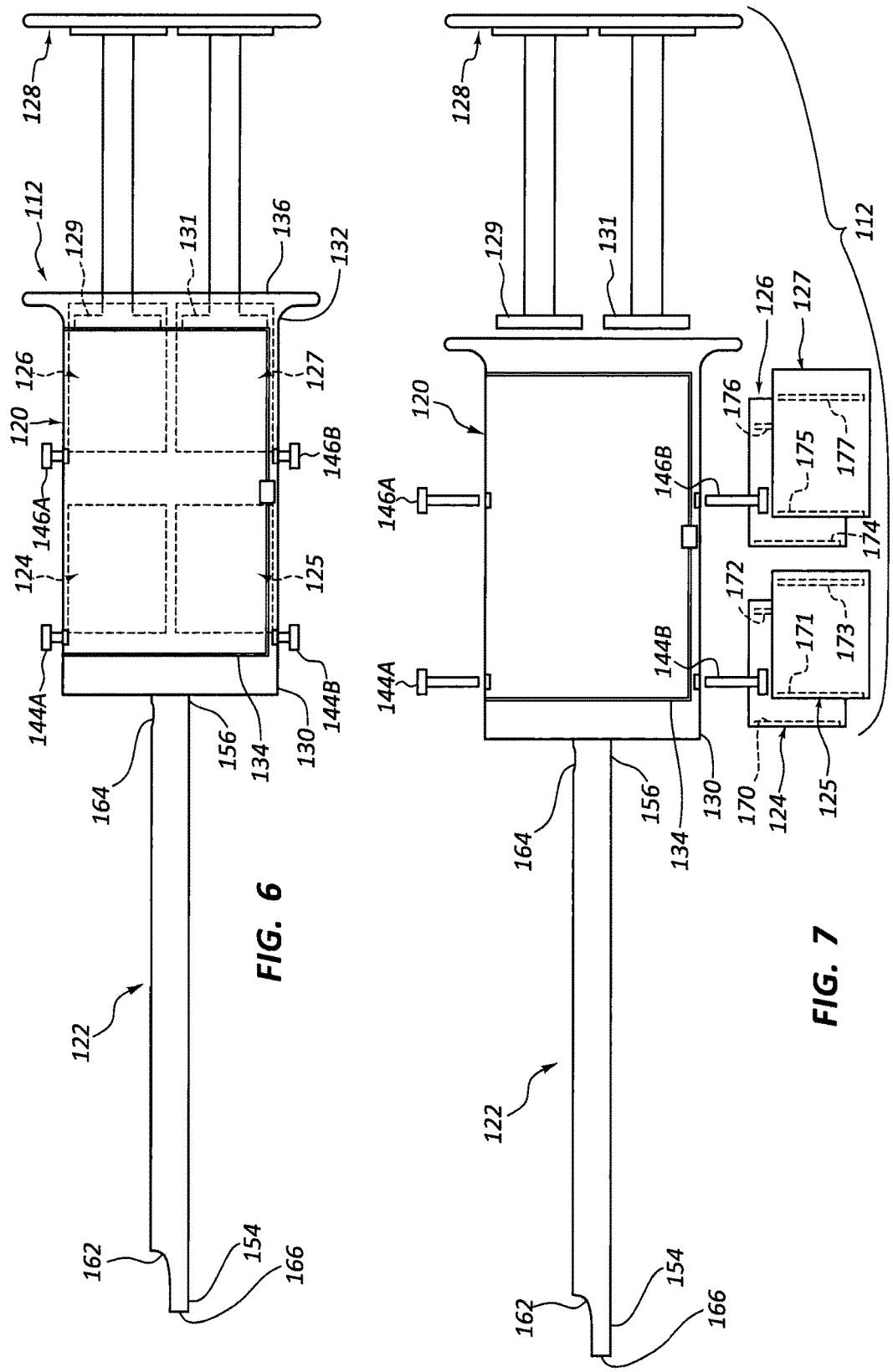

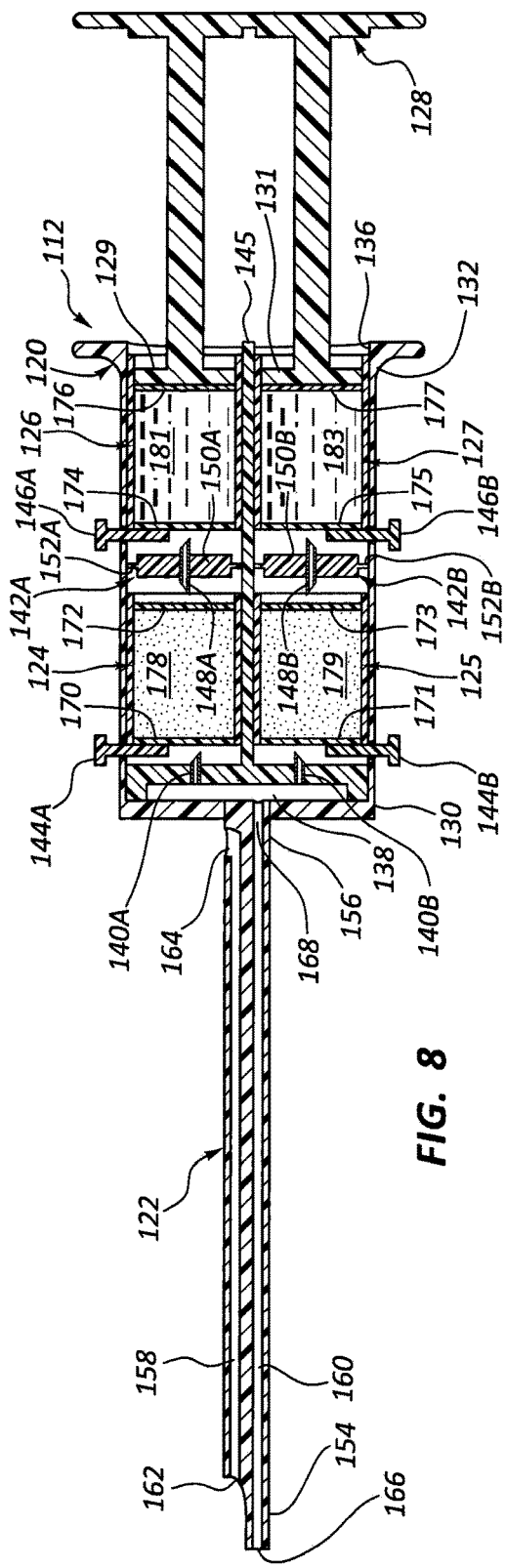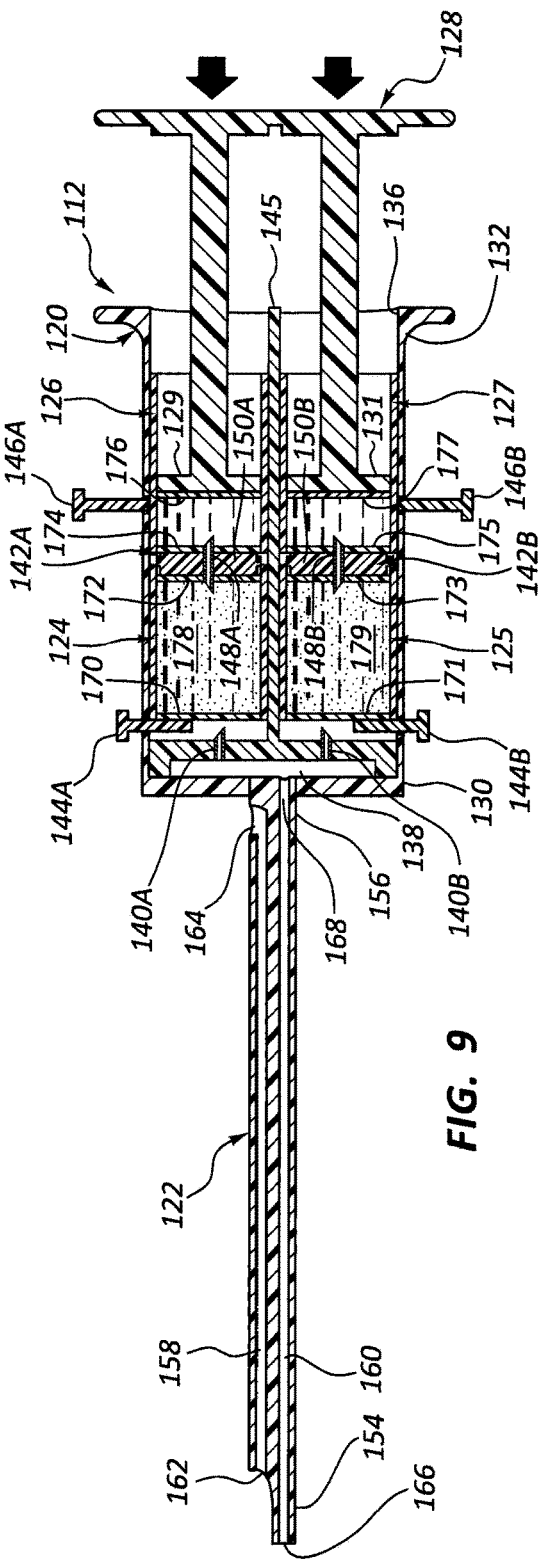
FIG. 8
FIG. 9

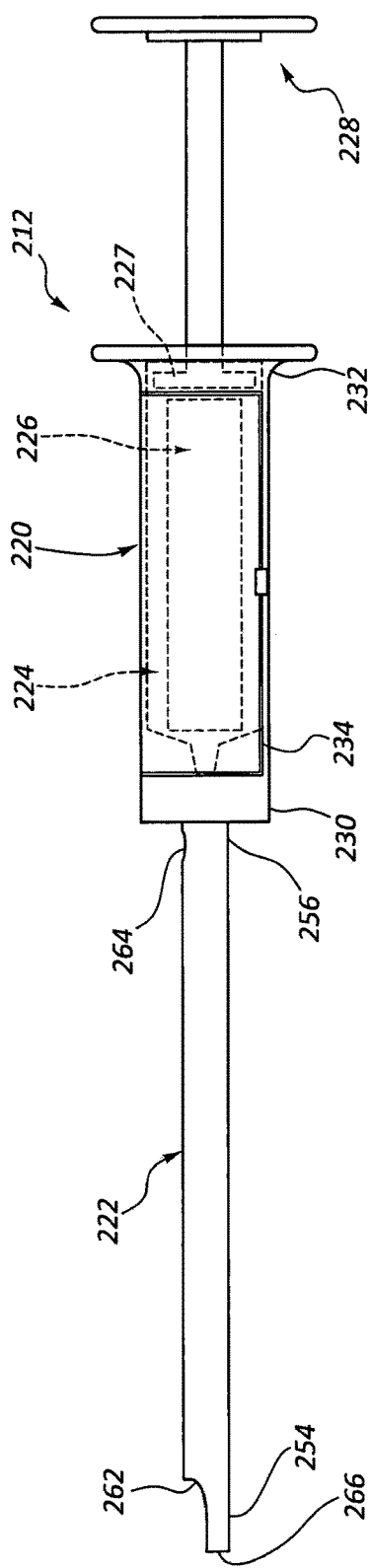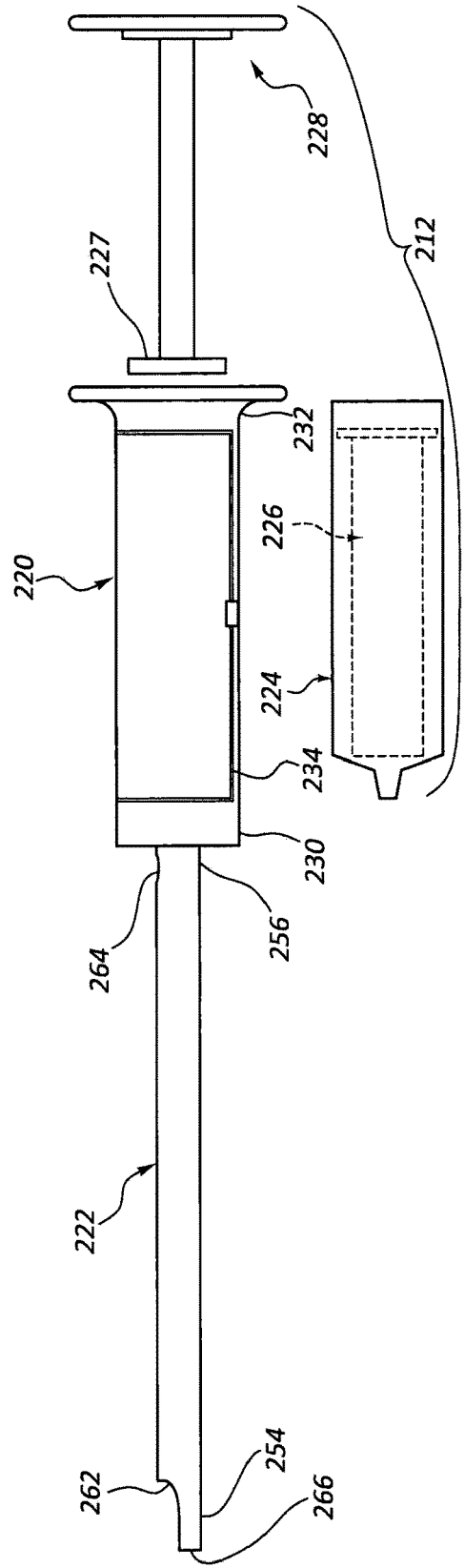
FIG. 11
FIG. 12

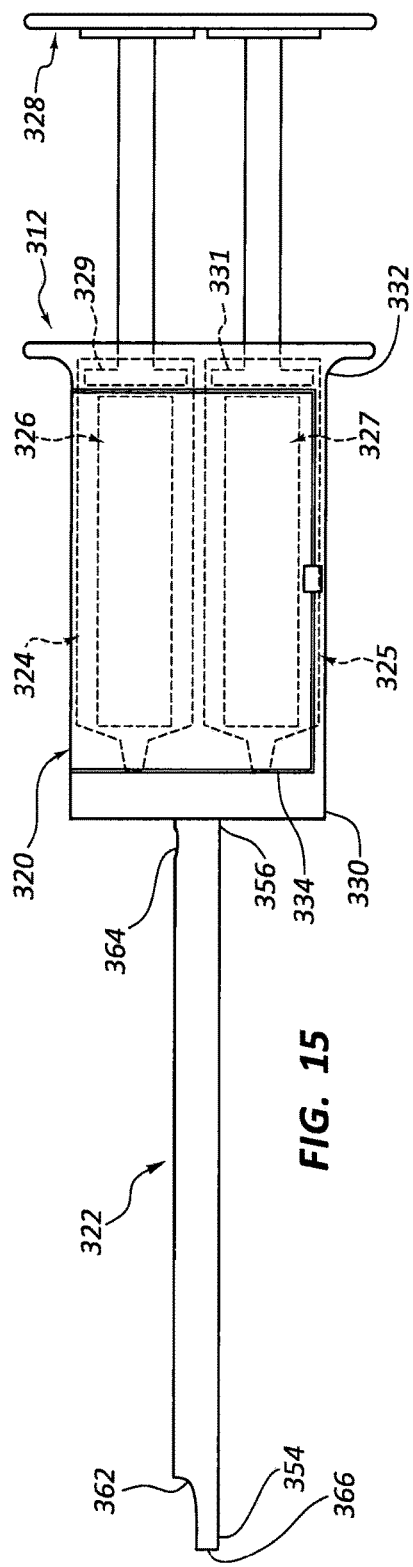
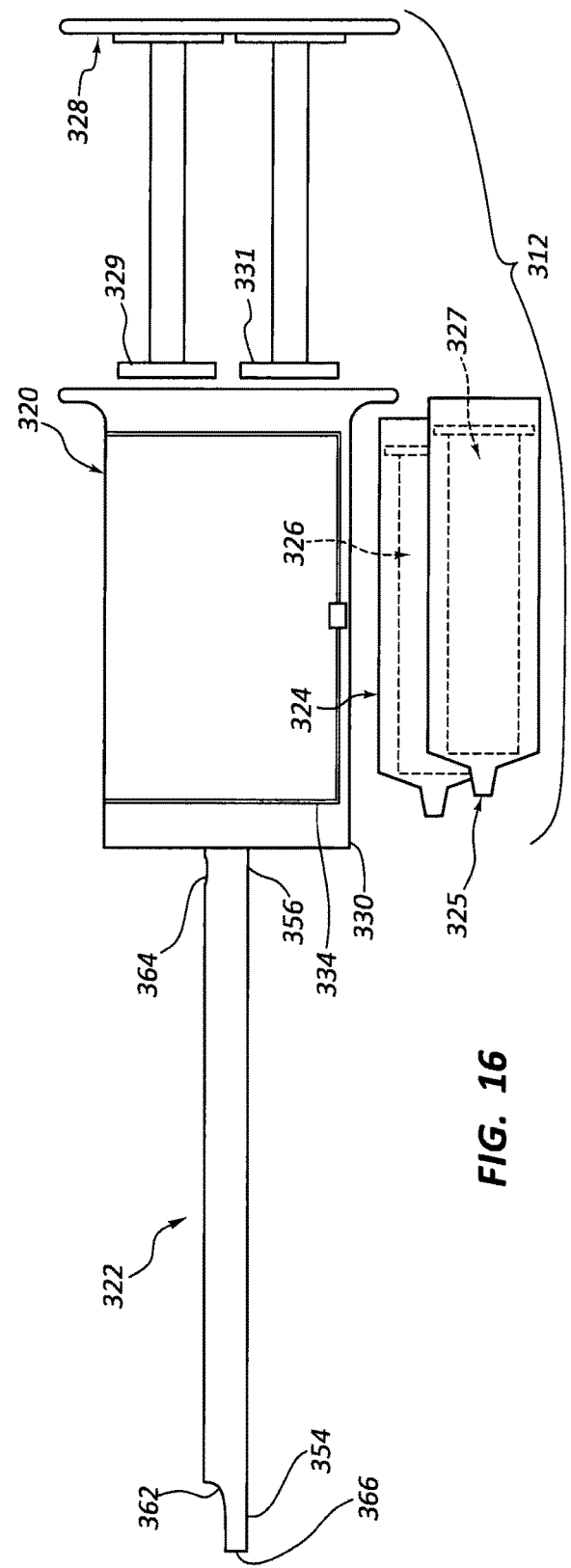

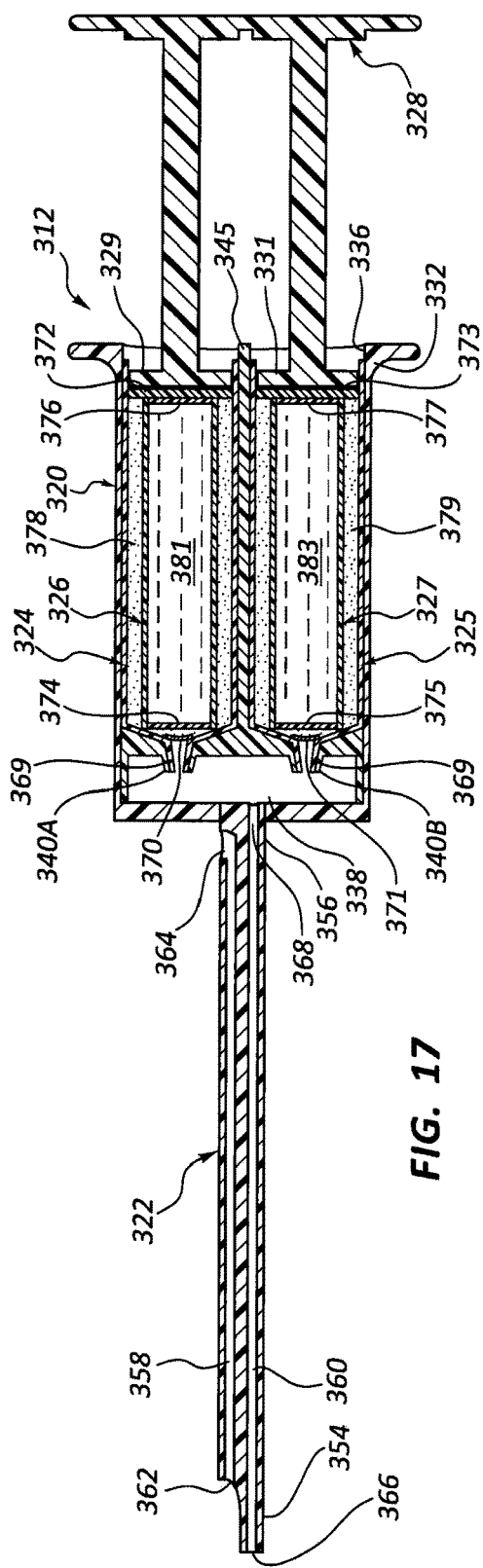
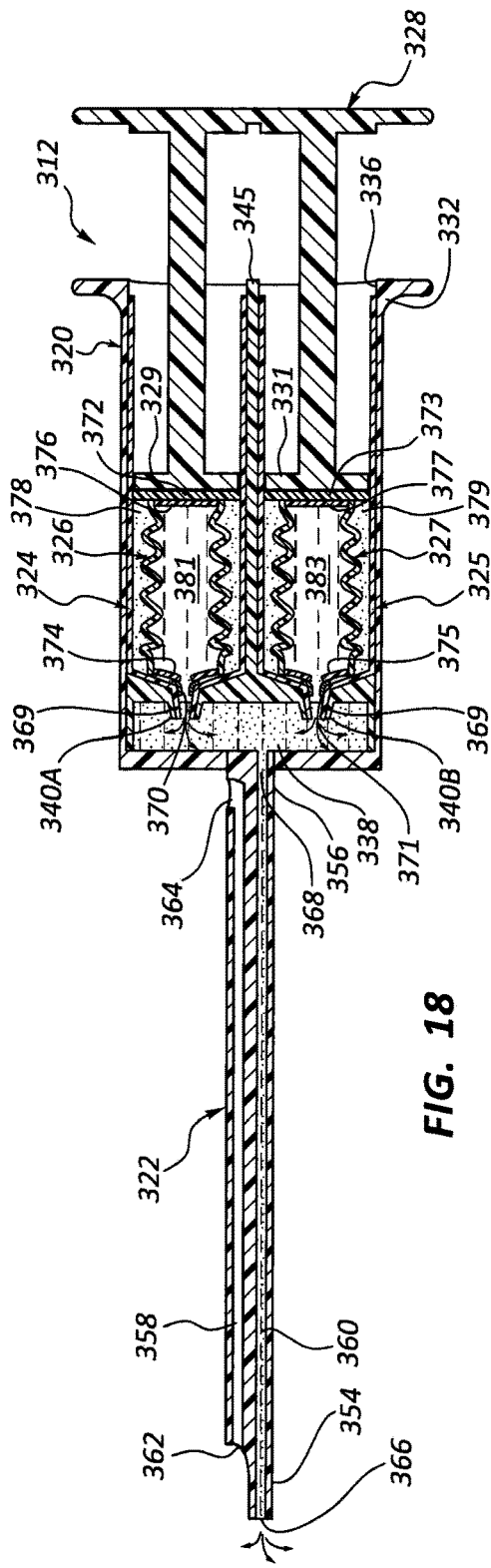
FIG. 17
FIG. 18

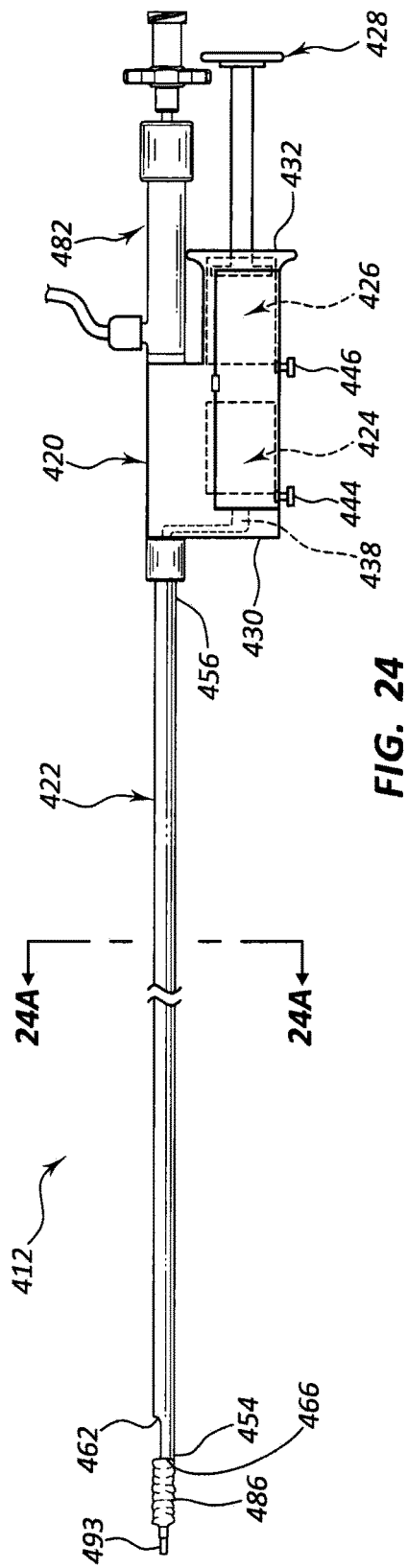
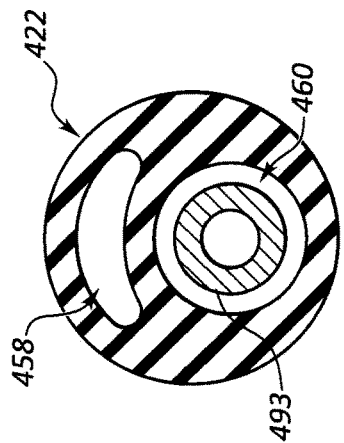
FIG. 24
FIG. 24A

SEALANT MIXING CONTAINERS FOR EXTRA VASCULAR BIOADHESIVE DELIVERY SYSTEMS AND METHODS

CROSS-REFERENCE TO RELATED APPLICATION

This application claims the benefit of the filing date of U.S. Provisional Application No. 61/622,865, filed 11 Apr. 2012, and entitled SEALANT MIXING CONTAINERS FOR EXTRA VASCULAR BIOADHESIVE DELIVERY SYSTEMS AND METHODS, the disclosure of which is incorporated, in its entirety, by reference.

TECHNICAL FIELD

The present disclosure relates generally to methods and systems for sealing tissue punctures, and more particularly, to methods and systems for mixing a bioadhesive sealant and delivering the mixed bioadhesive sealant to a tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

While there are a variety of prior art devices and techniques for closing such punctures, one primary problem is insuring a complete seal of the puncture. One technique includes the use of a bioadhesive material to seal the puncture. Some types of bioadhesive materials must be activated prior to use, and should be activated just prior to use in order to avoid premature activation of the bioadhesive material. The handling and activation of bioadhesive materials for use in vascular and other tissue puncture closure applications present a number of challenges, particularly when using bioadhesive sealant components that have a quick set time.

SUMMARY

One aspect of the present disclosure relates to a closure device operable to seal a vessel puncture. The closure device includes a delivery member and a sealant material applicator. The delivery member is insertable through a tissue tract to the vessel puncture. The sealant material applicator is configured to supply a volume of sealant material to the delivery member and includes a housing, a plunger assembly, and at least one container. The housing includes at least first and second chambers, wherein the first chamber carries a first sealant component of the sealant material and the second chamber carries a second sealant component of the sealant material. The plunger assembly includes at least first and second plunger members insertable into the first and second chambers, respectively. The at least one container is insertable into the first or second chamber and carries a third sealant component of the sealant material. The sealant material applicator is operable to create flow communication between the at least one container and at least one of the first and second chambers to mix the third sealant component with at least one of the first and second sealant components prior to creating the volume of sealant material.

The sealant material applicator may be operable to deliver the volume of sealant material through the delivery member and to the tissue tract to seal the vessel puncture from outside the vessel. The first sealant component may be carried in a first container, the second sealant component may be carried in a second container, and the third sealant component may be carried by a third container. Operating plunger assembly may create flow communication between the third container and the first container to combine the first and third sealant components prior to ejecting the volume of sealant material to the delivery member.

The first, second and third sealant components may be mixed within a mixing chamber of the sealant material applicator prior to being ejected from the sealant material applicator. The sealant material applicator may include at least one needle configured to create the flow communication. At least one of the first, second and third containers may include a frangible seal. The sealant material applicator may include a mixing chamber at a distal end thereof, wherein the first, second and third sealant components may be at least partially mixed in the mixing chamber before being ejected from the sealant material applicator as the sealant material. The at least one container may be positioned within the first chamber and exposed to the first sealant component, and operating the sealant material applicator ruptures the at least one container to create flow communication between the at least one container and the first chambers.

Another aspect of the present disclosure relates to a sealant material applicator that includes a housing, first and second sealant components, a first container, and a first mixing member. The housing includes a first chamber. The first sealant component is positioned in the chamber. The first container is positioned in the first chamber. The second sealant component is positioned in the first container. The mixing member is operable to provide flow communication between the first and second sealant components to mix the first and second sealant material components prior to ejecting the mixed first and second sealant components from the housing to seal a tissue puncture.

The first sealant component may be exposed to the second sealant component prior to creating the flow communication. The first container may include a rupturable seal. The sealant material applicator may include at least one needle configured to provide flow communication between the first container and the first sealant material component. The first container may be compressible upon operation of the mixing member to eject the second sealant component from the first container. The housing may include a second chamber having a third sealant component positioned therein, and a second container positioned in the second chamber, wherein the second container includes a fourth sealant component positioned therein, and operation of the mixing member mixes the third and fourth sealant materials. The sealant material applicator may include a mixing chamber, and operation of the mixing member moves the first, second, third and fourth sealant components into the mixing chamber for mixing together as a sealant material.

Another aspect of the present disclosure relates to a method of preparing a bioadhesive sealant for use in sealing a tissue puncture. The method includes providing a sealant applicator comprising a plunger assembly, a bioadhesive sealant having at least first, second and third sealant components, and a housing having first and second chambers. The first and second sealant components may be positioned in the first and second chambers, respectively, and the third sealant component may be carried by a first container that is positioned in the first chamber. The method also includes operating the plunger assembly to rupture a seal of the first container to combine the first and third sealant components, and ejecting the first, second and third sealants from the housing for use in sealing a tissue puncture.

The method may include operating the plunger assembly to mix the first, second and third sealant components prior to ejecting the bioadhesive sealant from the housing. The method may include carrying the first sealant component in a second container and carrying the second sealant component in a third container, and operating the plunger assembly ruptures a seal of the first, second and third containers prior to ejecting the bioadhesive sealant from the housing.

The bioadhesive sealant may further comprise a fourth sealant component carried by a second container that is positioned in the second chamber, and operating the plunger assembly ruptures a seal of the second container to combine the second and fourth sealant components. The housing may include a mixing chamber positioned distal of the first and second chambers, and operating the plunger assembly through a first operation step mixes the first and third sealant components, operating the plunger assembly through a second operation step mixes the first and third sealant components with the second sealant component in the mixing chamber, and operating the plunger assembly through a third operation step ejects the bioadhesive sealant from the housing.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example sealant delivery device in accordance with the present disclosure.

FIG. 2 is an exploded side view of the sealant delivery device of FIG. 1.

FIG. 3 is a cross-sectional view of the sealant delivery device of FIG. 1 in a position prior to mixing.

FIG. 4 is a cross-sectional view of the sealant delivery device of FIG. 1 in a first mixing position.

FIG. 6 is a side view of another example sealant delivery device in accordance with the present disclosure.

FIG. 7 is an exploded side view of the sealant delivery device of FIG. 6.

FIG. 8 is a cross-sectional view of the sealant delivery device of FIG. 6 in a position prior to mixing.

FIG. 9 is a cross-sectional view of the sealant delivery device of FIG. 6 in a first mixing position.

FIG. 11 is a side view of another example sealant delivery device in accordance with the present disclosure.

FIG. 12 is an exploded side view of the sealant delivery device of FIG. 11.

FIG. 15 is a side view of another example sealant delivery device in accordance with the present disclosure.

FIG. 16 an exploded side view of the sealant delivery device of FIG. 15.

FIG. 17 is a cross-sectional view of the sealant delivery device of FIG. 16 in a position prior to mixing.

FIG. 18 is a cross-sectional view of the sealant delivery device of FIG. 15 in a mixing position.

FIG. 24 is a side view of another example sealant delivery device in accordance with the present disclosure.

FIG. 24A is a cross-sectional view of the sealant delivery device of FIG. 24 taken along cross-section indicators 24A-24A.

Throughout the drawings, identical reference numbers designate similar, but not necessarily identical, elements.

DETAILED DESCRIPTION

Figure 5:
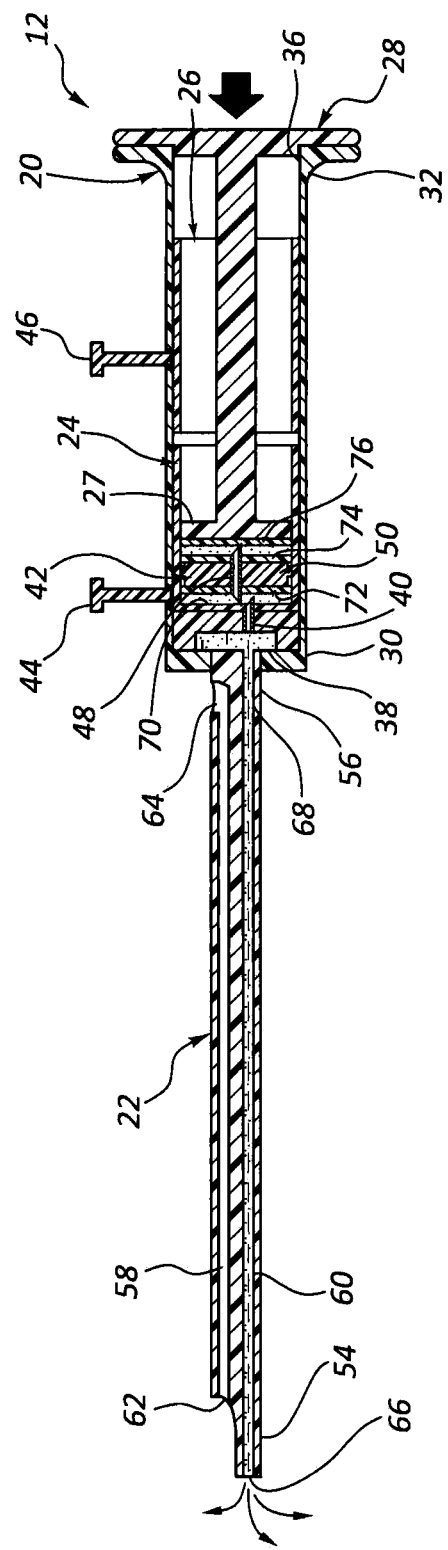
FIG. 5 is a cross-sectional view of the sealant delivery device of FIG. 1 in a second mixing position.
Figure 10:
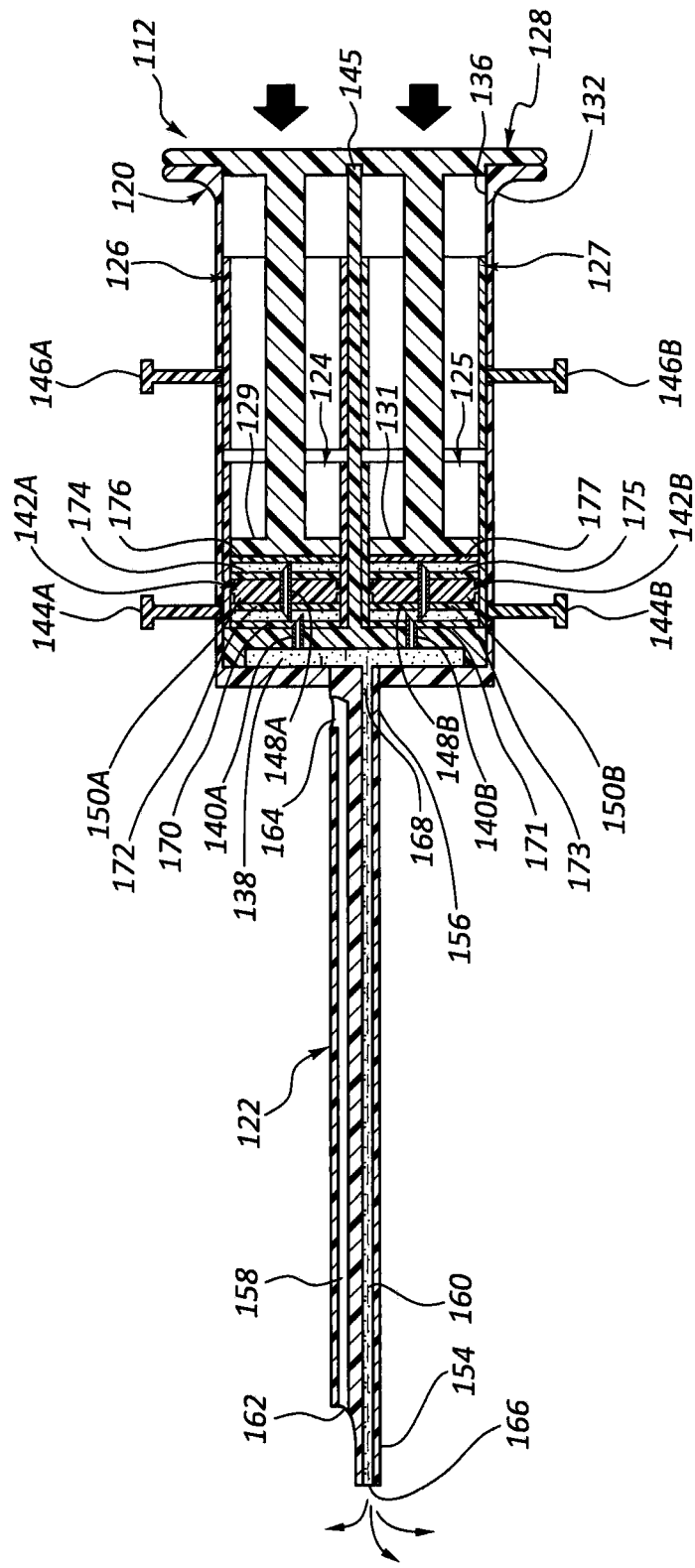
FIG. 10 is a cross-sectional view of the sealant delivery device of FIG. 6 in a second mixing position.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure includes a sealant delivery device that is used with a vascular closure system. The sealant delivery device may provide or deliver a volume of sealant to a tissue puncture (e.g., a vessel puncture) as part of sealing the tissue puncture with the vascular closure system. The sealant delivery device may operate to combine a plurality of sealant components together prior to delivering the sealant components as a sealant material used to seal the tissue puncture.

The sealant delivery device may include a housing portion configured to hold containers that carry the sealant components. The sealant containers may be arranged within the housing end-to-end (i.e., in a series arrangement). In some embodiments, at least one of the sealant containers is positioned within another one of the sealant containers. Typically, the sealant delivery device is operable to combine the sealant components of the various sealant containers within one or more of the containers in a pre-mixing step. The pre-mixing usually occurs prior to ejecting the sealant components through a delivery tube of the sealant delivery device to the tissue puncture.

The sealant delivery device may include a single chamber that holds a plurality of sealant containers. In other embodiments, the sealant delivery device includes a plurality of chambers wherein each chamber holds a plurality of sealant containers. The sealant delivery device may also include a mixing chamber used to mix sealant components outside of the sealant containers (e.g., the sealant components that have been pre-mixed in one of the sealant containers). In one example, the sealant delivery device includes two chambers, wherein each of the chambers holds at least two sealant containers and two or more sealant components are pre-mixed in each of the chambers. The pre-mixed sealant components are mixed again in the mixing chamber prior to being delivered through the delivery tube to the tissue puncture.

In one example, a first sealant container is positioned within a second sealant container, and the second sealant container is positioned in a housing of the sealant delivery device. The first sealant container holds a first sealant component, and the second sealant container holds a second sealant component. The first sealant container has a seal that is broken so that the first sealant component mixes with the second sealant component within the second sealant container. In one example, the first sealant container comprises a frangible seal that is broken by, for example, increasing pressure within the second sealant container or puncturing the first sealant container. In another example, the first sealant container has a seal that is broken by, for example, shaking, squeezing, twisting or heating the second sealant container. A seal of the first sealant container may be broken prior to inserting the second sealant container within the housing of the sealant delivery device. Alternatively, the seal of the first sealant container may be broken after positioning the second sealant container within the housing of the sealant delivery device by application of a force (e.g., via force applied by a plunger member of the sealant delivery device).

The sealant delivery device may include a plurality of flow connectors positioned within the housing that create flow communication between the sealant containers. The flow communication between the sealant containers may be in between the sealant containers in a mixing chamber of the housing in stages or steps. For example, moving a first sealant container relative to the second sealant container may create flow communication between the first and second sealant containers. In a second stage, moving the first and second sealant containers relative to the housing may create flow communication with a mixing chamber of the housing.

The sealant delivery device may include sliders or stops that hold the sealant containers in predetermined positions within the housing until the next step or stage of mixing. A plunger assembly may be used to move the sealant containers within the housing and create the desired flow communication and mixing (e.g., pre-mixing) of the sealant components carried by the sealant containers.

Referring now to FIGS. 1-5, an example sealant delivery device 12 includes a housing 20, a delivery tube 22, first and second sealant containers 24, 26, and a plunger assembly 28. The housing 20 is mounted to a proximal end of the delivery tube 22. The first and second sealant containers 24, 26 are positioned end-to-end within the housing 20. The plunger assembly 28 is operated to create flow communication between the sealant containers 24, 26 within the housing 20 and to eject the mixed sealant components carried by the sealant containers 24, 26 through the delivery tube 22 to a tissue puncture.

The sealant delivery device 12 is configured to operate in two separate stages. In a first stage, flow communication is created between the first and second sealant containers 24, 26 so that the sealant components carried by the first and second sealant containers 24, 26 may pre-mix to form a sealant material. In a second operational step, the sealant material is advanced through the delivery tube 22 to a tissue puncture. A third operational step may include moving the pre-mixed sealant components from the first and second sealant containers 24, 26 into a mixing chamber of the sealant delivery device 12 for further mixing prior to advancing the sealant material into the delivery tube 22.

In some arrangements, one or more of the first and second sealant containers 24, 26 may be integrally formed with the housing 20. For example, the first sealant container 24 may be formed at least in part by the housing 20. Typically, at least one of the first and second sealant containers 24, 26 is a separate, removable piece that is assembled with the housing 20.

The housing 20 may include distal and proximal ends 30, 32, an access opening 34, a plunger opening 36, a mixing chamber 38, first and second flow connectors 40, 42, and first and second sliders 44, 46. The delivery tube 22 is connected at the distal end 30 of the housing 20. The access opening 34 may provide access into the housing 20 for inserting the first and second sealant containers 24, 26. The access opening 34 may be positioned along a length of the housing 20 at a location spaced between the distal and proximal ends 30, 32. The access opening 34 may provide lateral insertion of the first and second sealant containers 24, 26 into the housing 20. In other arrangements, the access opening 34 may be positioned at one of the distal and proximal ends 30, 32 and provide longitudinal insertion of at least one of the first and second sealant containers 24, 26.

The access opening 34 may include a door that is opened and closed to gain access to an interior of the housing 20.

The plunger opening 36 may provide an opening through which the plunger assembly 28 extends into the housing 20. A plunger opening 36 may be configured to help retain the plunger assembly 28 assembled with the housing 20. In other arrangements, the plunger opening 36 may be configured to permit removal of the plunger assembly 28 from the housing 20 as part of, for example, inserting the first and second sealant containers 24, 26 into housing 20.

Mixing chamber 38 may be positioned at the distal end 30 and connected in flow communication with a lumen of delivery tube 22. The first flow connector 40 may be in flow communication with mixing chamber 38. First flow connector 40 may include, for example, a needle, breakable seal, a luer seat, or other connection feature that provides the desired flow communication with mixing chamber 38. In some arrangements, first flow connector 40 may be in direct flow communication with a lumen of delivery tube 22 and the mixing chamber 38 is removed.

Second flow connector 42 may be positioned between the first and second sealant containers 24, 26 when sealant delivery device 12 is assembled and ready for use. Second flow connector 42 may include a carrier 50 that holds a second needle 48. The second needle 48 may create flow communication between first and second sealant containers 24, 26. In some arrangements, second flow connector 42 is directly mounted to one of the first and second sealant containers 24, 26. In other arrangements, second flow connector 42 is mounted to a wall of housing 20 using, for example, a breakable mount 52. Breakable mount 52 may suspend carrier 50 and second needle 48 in a position spaced out of contact from the first and second sealant containers 24, 26 until such time as the plunger assembly 28 is operated to create flow communication between the first and second sealant containers 24, 26.

The first and second sliders 44, 46 may suspend the first and second sealant containers 24, 26, respectively, from contact with the first and second flow connectors 40, 42. The first and second sliders 44, 46 may be operated as part of a multi-stage mixing of the sealant components carried by the first and second sealant containers 24, 26. For example, first and second sliders 44, 46 may be maintained in an inserted position shown in FIG. 3 until the operator is ready to pre-mix the sealant components of the first and second sealant containers 24, 26. FIG. 4 shows the second slider 46 removed into a withdrawn position so that second sealant container 26 may move axially relative to first sealant container 24. Moving the plunger assembly 28 distally to advance a first plunger member 27 of the plunger assembly 28 may advance the second sealant container 26 relative to first sealant container 24 to puncture the second needle 48 through portions of the first and second sealant containers 24, 26 to create flow communication. Further distal movement of the plunger assembly 28 forces a sealant component carried by the second sealant container 26 into the first sealant container 24.

The first slider 44 may be withdrawn to permit the first sealant container 24 to advance and be punctured by the first flow connector 40 (i.e., a needle) to create flow communication between first sealant container 24 and mixing chamber 38. Further advancing first plunger member 27 forces the pre-mixed sealant components held in first sealant container 24 to move into mixing chamber 38 and through delivery tube 22 to a tissue puncture.

Delivery tube 22 includes distal and proximal ends 54, 56, and first and second lumens 58, 60. First lumen 58 includes distal and proximal openings 62, 64. Second lumen 60 includes distal and proximal openings 66, 68. First lumen 58 may be configured for mounting of sealant delivery device 12 to another device such as, for example, a balloon inflation device of a vascular closure system, as will described in further detail below. The distal and proximal opening 62, 64 may be part of a rapid exchange system for mounting sealant delivery device 12 to another device. In some arrangements, delivery tube 22 includes only the second lumen 60, which is used to deliver sealant material to a tissue puncture. The proximal opening 68 of second lumen 60 is connected in flow communication with mixing chamber 38. A distal opening 66 is positioned at a distal end of sealant delivery device 12 and typically positioned adjacent to a tissue puncture for delivery of a sealant to a tissue puncture.

First sealant container 24 includes first distal and proximal seals 70, 72. Second sealant container 26 includes second distal and proximal seals 74, 76. First sealant container 24 holds a first sealant component 78. Second sealant container 26 holds a sealant component 81. Typically, the first and second sealant components 78, 81 are pre-mixed within first sealant container 24 upon operating plunger assembly 28 as shown in FIG. 4. The mixed first and second sealant components 78, 81 are then advanced into mixing chamber 38 and through delivery tube 22 to a tissue puncture upon further operation of plunger assembly 28 as shown in FIG. 5.

In other arrangements, second sealant component 81 is held under vacuum such that creating flow communication using second flow connector 42 (e.g., by operation of plunger assembly 28 moving second sealant container 26 axially toward first sealant container 24). Once the first and second sealant containers 24, 26 are connected in flow communication, the vacuum pressure within second sealant container 26 draws the first sealant component 78 into second sealant container 26 for mixing of the first and second sealant components 78, 81. The plunger assembly 28 may then be further operated to eject the mixed first and second sealant components 78, 81 through the first and second sealant containers 24, 26 and delivery tube 22 to the tissue puncture.

Many variations of sealant delivery device 12 may be possible. One variation includes operation without the first and second sliders 44, 46, or integration of the first and second sliders 44, 46 into housing 20. Other connection features besides needles may be used for first and second flow connectors 40, 42. Generally, sealant delivery device 12 is operable to create pre-mixing of sealant components within containers that have been mounted to the sealant delivery device (e.g., mounted within housing 20). The pre-mixing may occur outside of a mixing chamber of the housing, such as outside of the housing in a mixing operation separate from the housing 20 and plunger assembly 28. The sealant containers may be arranged end-to-end or in series. The pre-mixing may occur as one mixing step in a series of mixing and delivery steps using the sealant delivery device 12, and may be followed by mixing with other sealant components in a secondary mixing step.

Another example sealant delivery device 112 is shown and described with reference to FIGS. 6-10. Sealant delivery device 112 includes a housing 120 having multiple chambers. The chambers may be defined in part by a dividing wall 145. Each of the chambers may hold at least one sealant container carrying a sealant component. Pre-mixing of sealant components may occur in each of the chambers of housing 120. The housing 120 may also include features (e.g., a mixing chamber) that provide mixing of the pre-mixed sealant components prior to ejecting the sealant material through a sealant delivery tube 122 to a tissue puncture.

Housing 120 includes distal and proximal ends 130, 132, an access opening 134, a plunger opening 136, a mixing chamber 138, first flow connectors 140A,B, second flow connectors 142A,B, first and second sliders 144A,B and 146A,B. The first and second flow connectors 140A, 142A may be associated with one of the chambers in housing 120, and a second set of first and second flow connectors 140B, 142B may be associated with a second chamber of the housing 120. First and second sliders 144A, 146A may be associated with one of the chambers, while a second set of first and second sliders 144B, 146B may be associated with another of the chambers of housing 120.

Sealant delivery device 112 also includes a delivery tube 122 having distal and proximal ends 154, 156 and first and second lumens 158, 160. The first lumen 158 includes distal and proximal openings 162, 164. The second lumen 160 includes distal and proximal openings 166, 168. First lumen 158 is configured for mounting the sealant delivery device 112 to a second device such as, for example, a balloon inflation device or a guidewire as part of, for example, a rapid exchange mounting system. The second lumen 160 is connected in flow communication with the mixing chamber 138 to receive a volume of sealant material for delivery to a tissue puncture.

Sealant delivery device 112 also includes first and second sealant containers 124, 126 positioned in a first chamber of housing 120, and third and fourth sealant containers 125, 127 positioned in a second chamber of housing 120. First sealant container 124 includes first distal and proximal seals 170, 172. Second sealant container 126 includes second distal and proximal seals 174, 176. Third sealant container 125 includes third distal and proximal seals 171, 173. Fourth sealant container 127 includes fourth distal and proximal seals 175, 177. The first and second sealant containers 124, 126 carry first and second sealant components 178, 181, respectively. Third and fourth sealant containers 125, 127 carry third and fourth sealant components 179, 183, respectively. In at least some arrangements, the first and second sealant components 178, 181 may be the same, and the third and fourth sealant components 179, 183 may be different from each other. In some arrangements, one of the first, second, third and fourth sealant containers 124, 126, 125, 127 is empty.

A plunger assembly 128 includes first and second plunger members 129, 131 associated with each chamber and a set of sealant containers held in housing 120. In a first operational step, after inserting the first, second, third and fourth sealant containers 124, 126, 125, 127 into housing 120 and the second sliders 146A,B are removed, the plunger assembly 128 is operated to create flow communication between the first and second sealant containers 124, 126 using second flow connector 142A, and third and fourth sealant containers 125, 127 are connected in flow communication using second flow connector 142B. Further advancing the plunger assembly 128 moves the second and fourth sealant components 181, 183 into the first and third sealant containers 124, 125, respectively. The first and second sealant components 178, 181 are pre-mixed and the third and fourth sealant components 179, 183 are pre-mixed.

Further operating plunger assembly 128 in a second step, after removing first sliders 144A,B, creates flow communication between the first and third sealant containers 124, 125 and mixing chamber 138 via the first flow connectors 140A,B. Still further advancing plunger assembly 128 moves the pre-mixed sealant components into mixing chamber 138 for further mixing and ejection into delivery tube 122 for delivery to a tissue puncture.

Variations of the sealant delivery device 112 may include, for example, three or more chambers that each includes at least one sealant container. The sealant components carried in each chamber may be mixed in a further operational step within the housing prior to ejection through the delivery tube. Various connection features may be used to create flow communication between the sealant containers and the delivery tube. For example, in addition to using needles, luer connectors and other connection features may be used.

Referring now to FIGS. 11-14, another example sealant delivery device 212 includes a housing 220, a delivery tube 222, first and second sealant containers 224, 226, and a plunger assembly 228. Housing 220 may include proximal and distal ends 230, 232, an access opening 234, a plunger opening 236, a mixing chamber 238, and a first flow connector 240. Housing 220 may include a single chamber sized to receive at least one sealant container. In some arrangements, the housing 220 may include a direct channel or flow path between first flow connector 240 and a lumen of delivery tube 222, and be structured without the mixing chamber 238.

First flow connector 240 may include a connection seat such as a luer fitting. Mounting the first sealant container 224 within housing 220 may include creating a fluid-tight seal between first flow connector 240 and a connection feature of first sealant container 224. Alternatively, a needle or other device may be used to create the desired flow communication between mixing chamber 238 and an interior of first sealant container 224. The first sealant container 224 may be inserted into housing 220 via the access opening 234. The plunger assembly 228 is inserted through the plunger opening 236.

Delivery tube 222 may include distal and proximal ends 254, 256, and first and second lumens 258, 260. First lumen 258 includes distal and proximal openings 262, 264. Second lumen 260 includes distal and proximal openings 266, 268. First lumen 258 may be configured to mount sealant delivery device 212 to another device such as, for example, a balloon inflation device or a guidewire using rapid exchange features. In some examples, delivery tube 222 includes only the second lumen 260 for delivery of a sealant material to a tissue puncture.

Proximal opening 268 of second lumen 260 is connected in flow communication with mixing chamber 238. Distal opening 266 is arranged for delivering a volume of sealant material to a tissue puncture.

First sealant container 224 includes first distal and proximal seals 270, 272. Second sealant container 226 includes second distal and proximal seals 274, 276. First sealant container 224 carries a first sealant component 278. Second sealant container 226 carries a second sealant component 281.

First sealant container 224 may also include a connector such as a luer connector 269 for connection to the first flow connector 240 of housing 220. First distal seal 270 may control fluid access to luer connector 269. First distal seal 270 may be removed in some embodiment, or may comprise a frangible seal that ruptures when exposed to a threshold pressure condition.

Figure 13:
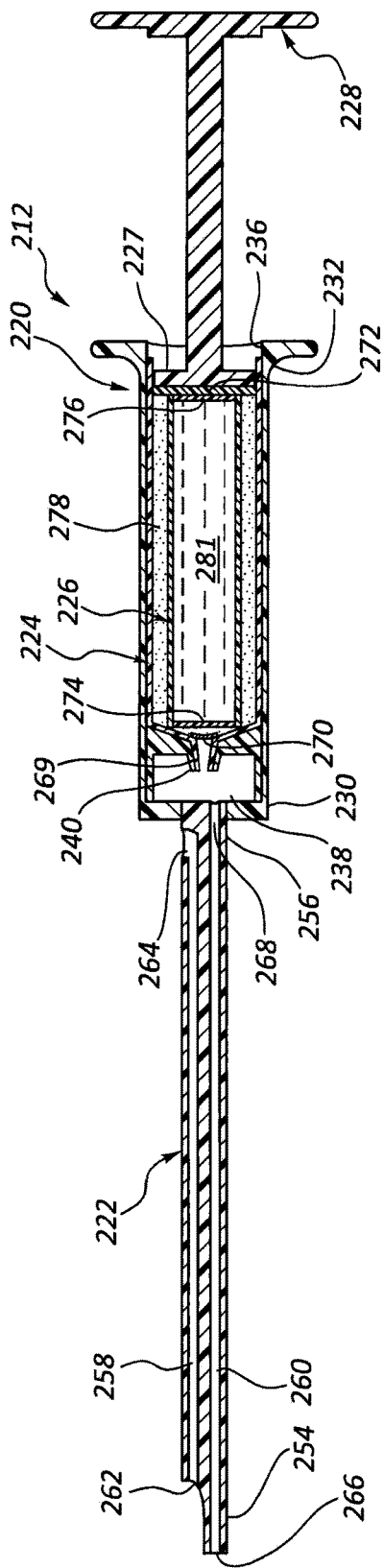
FIG. 13 is a cross-sectional view of the sealant delivery device of FIG. 11 in a position prior to mixing.
Figure 13A:
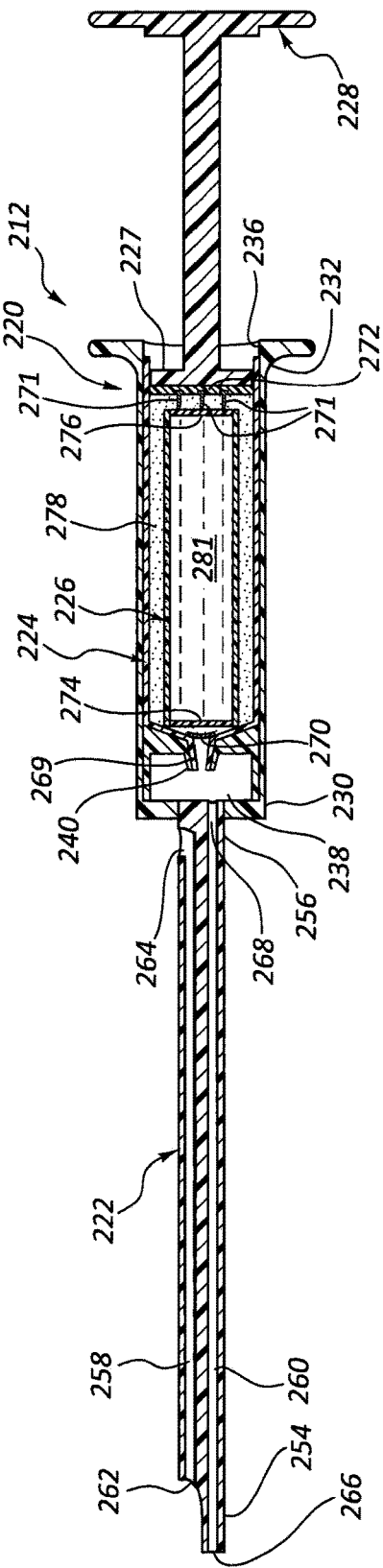
FIG. 13A is a cross-sectional view of the sealant delivery device of FIG. 11 in a position prior to mixing using a piercing member to rupture one of the sealant containers.

Second sealant container 226 is positioned within first sealant container 224. Second sealant container 226 may be configured to release its contents thereby allowing the first and second sealant components 278, 281 to pre-mix within first sealant container 224. The second sealant container 226 may be punctured using at least one puncture member 271 as shown in FIG. 13A. The puncture members 271 may be connected to one of the proximal seal 272 and a first plunger member 227 of plunger assembly 228. Advancing the plunger assembly 228 may cause the puncture members 271 to rupture the second sealant container 226. In another example, an increased pressure condition within first sealant container 224 may cause the second sealant container 226 to rupture. In still further arrangements, bending, squeezing, or twisting the first sealant container 224 may cause the second sealant container 226 to rupture.

Forces may be applied to the first sealant container 224 to rupture the second sealant container 226 prior to inserting the first sealant container 224 within housing 220. Alternatively, advancing plunger assembly 228 while the first and second sealant containers 224, 226 are positioned within housing 220 may apply force to an exterior of first sealant container 224 (i.e., the squeezing, bending or twisting described above) to rupture the second sealant container 226. In still further arrangements, the housing 220 may include a flexible portion that permits application of a squeezing, bending or twisting force to the first sealant container 224 while the first sealant container 224 is positioned within housing 220.

Figure 14:
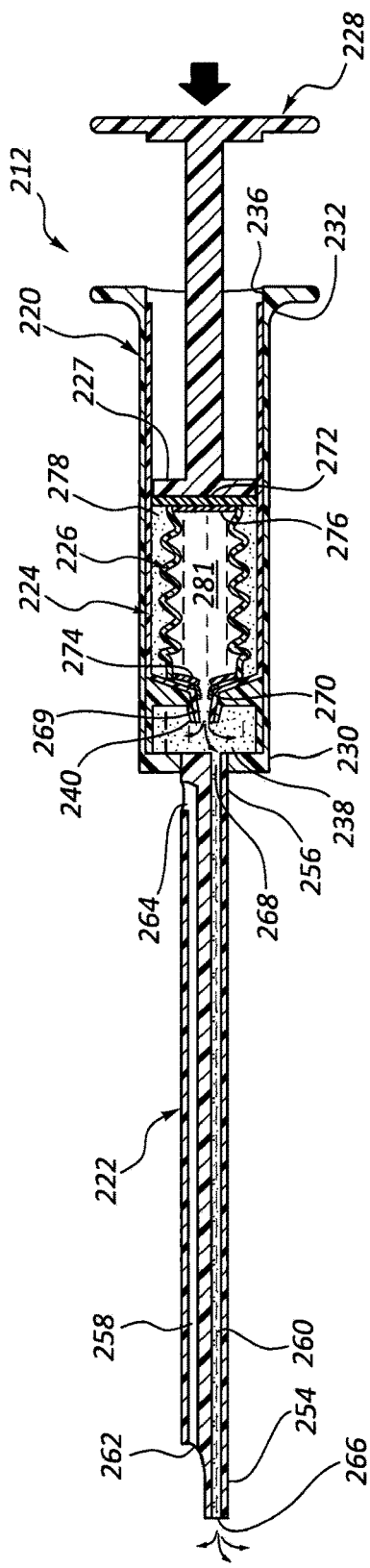
FIG. 14 is a cross-sectional view of the sealant delivery device of FIG. 11 in a mixing position.

After pre-mixing of the first and second sealant components 278, 281 within first sealant container 224, further operation of plunger assembly 228 may force the pre-mixed first and second sealant components 278, 281 into the mixing chamber 238 and through delivery tube 222 to a tissue puncture. FIG. 14 shows the first plunger member 227 advanced through the first sealant container 224 to force first and second sealant components 278, 281 out of first sealant container 224. This advancing of first plunger member 227 may also compress the second sealant container 226.

Other devices or features may be used in place of plunger assembly 228 to cause the second sealant container 226 to expel its contents within first sealant container 224 and eject the pre-mixed first and second sealant components 278, 281 into mixing chamber 238. For example, a roller (e.g., a roller connected to a distal end of a plunger member) may be moved within housing 220 to apply a force to first sealant container 224. In another example, the housing 220 is compressible or may be flexible to facilitate rolling up, twisting, or squeezing of the housing 220 to create the desired rupture of second sealant container 226 and ejection of sealant material from first sealant container 224.

Referring now to FIGS. 15-18, another example sealant delivery device 312 is shown including multiple chambers defined within a housing 320 using, for example, a dividing wall 345. Each chamber of housing 320 may carry a plurality of sealant containers. Sealant delivery device 312 includes a housing 320, a delivery tube 322, first and second sealant containers 324, 326, third and fourth sealant containers 325, 327, and a plunger assembly 328. Housing 320 includes distal and proximal ends 330, 332, an access opening 334, a plunger opening 336, a mixing chamber 338, and first flow connectors 340A,B. The first flow connectors 340A,B may include, for example, a luer connection seat that provides a fluid-tight connection with first and third sealant containers 324, 325, respectively. In some arrangements, the housing 320 does not include mixing chamber 338 and provides direct flow communication between first flow connectors 340A,B and a lumen of delivery tube 322.

Delivery tube 322 includes distal and proximal ends 354, 356, and first and second lumens 358, 360. First lumen 358 includes distal and proximal openings 362, 364. Second lumen 360 includes distal and proximal openings 366, 368. First lumen 358 may be configured to mount the sealant delivery device 312 to another device such as, for example, a balloon inflation device or a guidewire as part of a rapid exchange arrangement. In some embodiments, the delivery tube 322 only includes the second lumen 360 for delivery of a sealant material to a tissue puncture.

First sealant container 324 includes first distal and proximal seals 370, 372. Second sealant container 326 is positioned within first sealant container 324 and includes second distal and proximal seals 374, 376. First sealant container 324 carries a first sealant component 378. Second sealant container 326 carries a second sealant component 381.

Third sealant container 325 includes third distal and proximal seals 371, 373. Fourth sealant container 327 includes fourth distal and proximal seals 375, 377 and is positioned within the third sealant container 325. Third sealant container 325 carries a third sealant component 379. Fourth sealant container 327 carries a fourth sealant component 383.

The housing 320 and first, second, third and fourth sealant containers 324, 326, 325, 327 may operate in a similar way and have similar features to the sealant delivery device 212 described above. The sealant delivery device 312 may operate to provide pre-mixing of first and second sealant components 378, 381 and third and fourth sealant components 379, 383 prior to mixing all of the first, second, third and fourth sealant components 378, 381, 379, 383 within mixing chamber 338. The pre-mixing within first and third sealant containers 324, 325, mixing within mixing chamber 338, and ejection through delivery tube 322 to a tissue puncture may occur by operating plunger assembly 328. In some arrangements, plunger assembly 328 provides only some of the pre-mixing, mixing and ejection functions for sealant delivery device 312. For example, the pre-mixing may occur at least in part (e.g., rupturing of the second and fourth sealant containers 326, 327) outside of housing 320.

As described above with reference to sealant delivery device 212, other features and methods of rupturing seals, pre-mixing and ejecting sealant components may be used in place or in combination with a plunger assembly 328 having first and second plunger members 329, 331. For example, rollers, puncture members, compressible housing walls, and other features may be used. Sealant delivery devices having three or more chambers, which each include at least one sealant container, may be used to mix multiple sealant components, or provide a sequence of pre-mixing and mixing that is not possible with one or two chambers.

Figure 19:
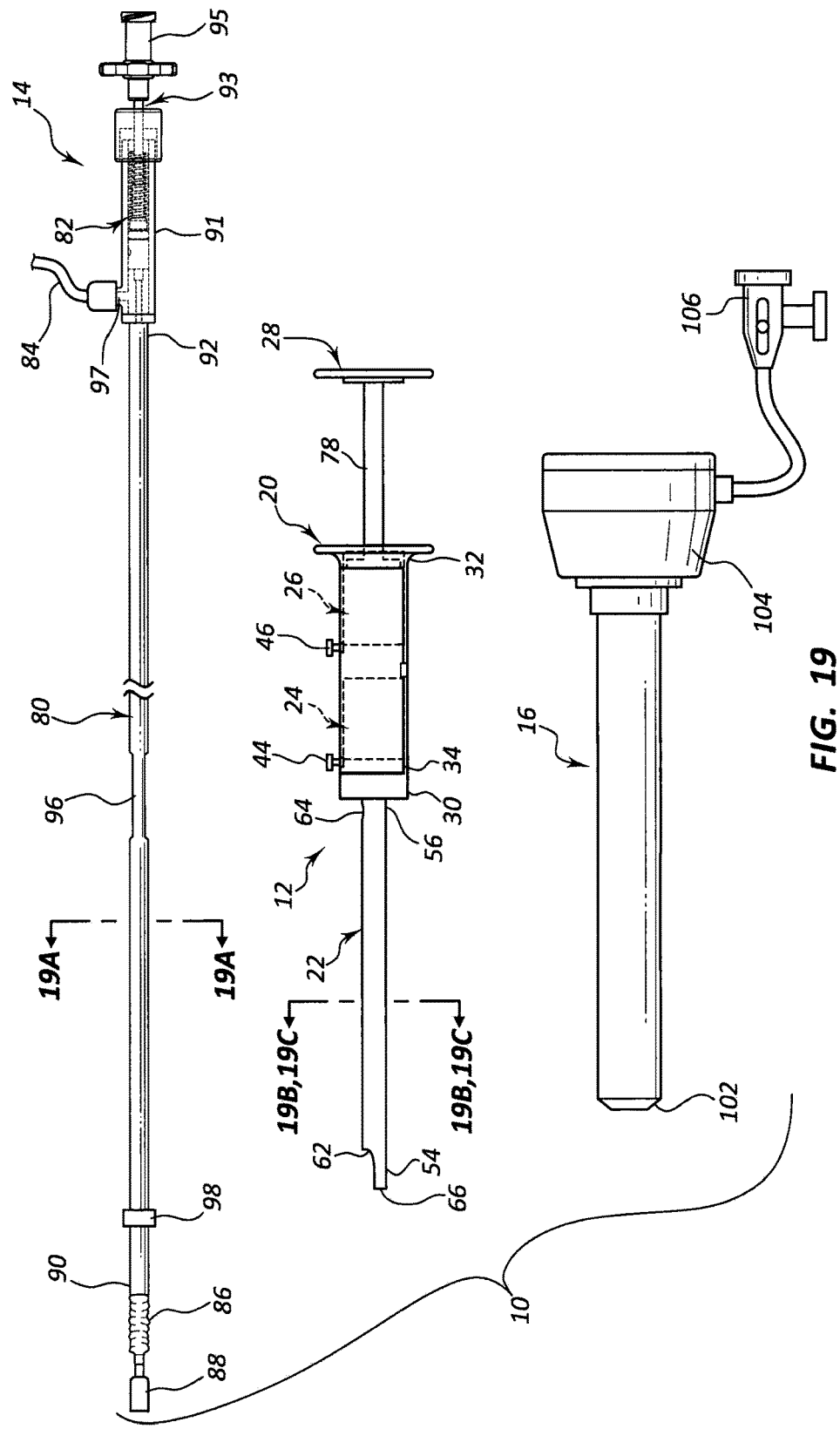
FIG. 19 is a side view of an example vascular closure system that includes the sealant delivery device of FIG. 1.
Figure 19A:
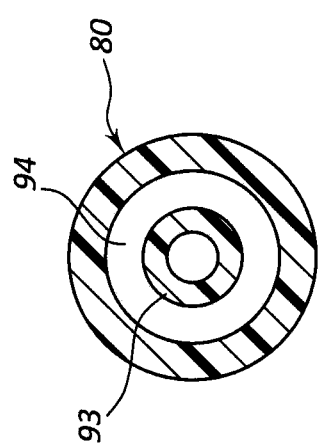
FIG. 19A is a cross-sectional view of a balloon inflation device of the vascular close system of FIG. 19 taken along cross-section indicators 19A-19A.
Figure 19B:
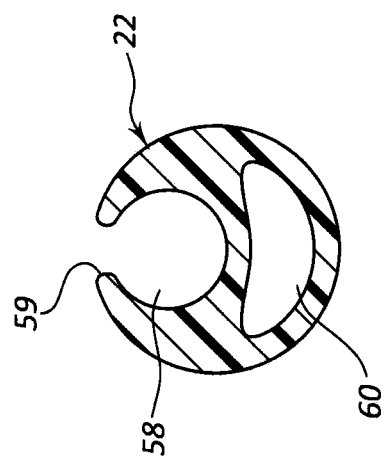
FIGS. 19B-C are cross-sectional views of the sealant delivery device of FIG. 19 taken along cross-section indicators 19B,19C-19B,19C.
Figure 19C:
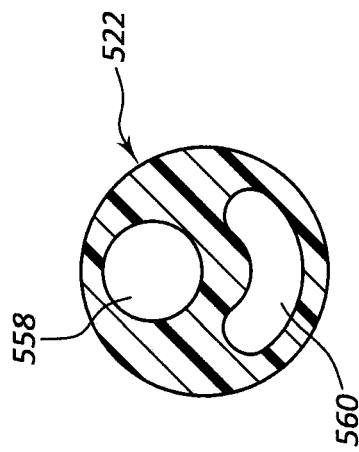

Referring now to FIG. 19, an example vascular closure system 10 is shown including the sealant delivery device 12, a balloon inflation device 14, and a sheath 16. FIG. 19B shows a cross-section of sealant delivery device 12. The first lumen 58 may include a side opening 59 that provides lateral access to the first lumen 58. Side opening 59 may assist in mounting the sealant delivery device 12 to the balloon inflation device 14. FIG. 19C shows an alternative construction for a delivery tube 522 having a first lumen 558 that is closed around its periphery, and a second lumen 560. Either of the delivery tube constructions shown in FIGS. 19B and 19C may be used for the sealant delivery device 12.

The balloon inflation device includes an inflation tube 80, a balloon location device 82, an inflation source 84, a balloon 86, and a detachable tip 88. The inflation tube 80 may include distal and proximal ends 90, 92, an inflation lumen 94, an exchange port 96, and a collar 98 (see FIGS. 19 and 19A). Lumen location device 82 may include a housing 91, an inner tube 93, an inner tube manifold 95, and an inflation port 97 (see FIGS. 19 and 19A). The inner tube 93 may extend through the inflation lumen 94 of the inflation tube 80 through location distal of the distal end 90 of inflation tube 80. Balloon 86 may be coupled at its proximal end to the inflation tube 80 and connected at its distal end to inner tube 93. Inner tube 93 may move axially relative to housing 91 upon inflation of balloon 86 to provide a visual indicator to the operator of a condition of the balloon 86 (e.g., an inflation pressure or a size of balloon 86). Detachable tip 88 may be connected at a distal end of inner tube 93.

Sheath 16 may include a distal end 102, a hub 104, and an injection port 106. In operation, the balloon inflation device 14 is advanced through the sheath 16, and the balloon inflation device 14 and sheath 16 are advanced through a tissue tract to a tissue puncture. In a later step, the sealant delivery device 12 may be advanced along the balloon inflation device 14 to the tissue puncture for delivery of a sealant carried by first and second sealant containers 24, 26 to seal the tissue puncture.

Figure 20:
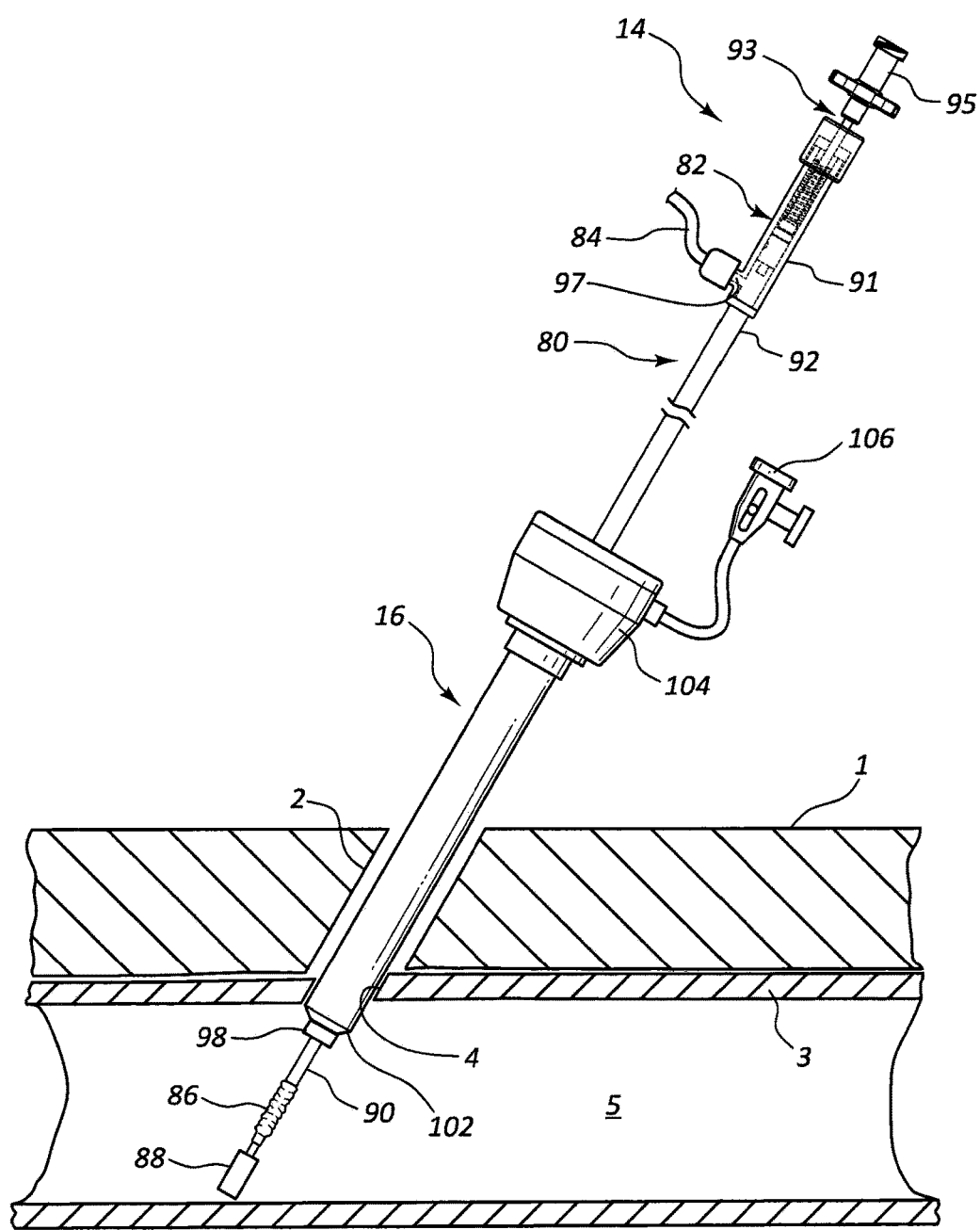
FIGS. 20-23 show steps of operating the vascular closure system of FIG. 19 to close a vessel puncture.
Figures 21, 21A:
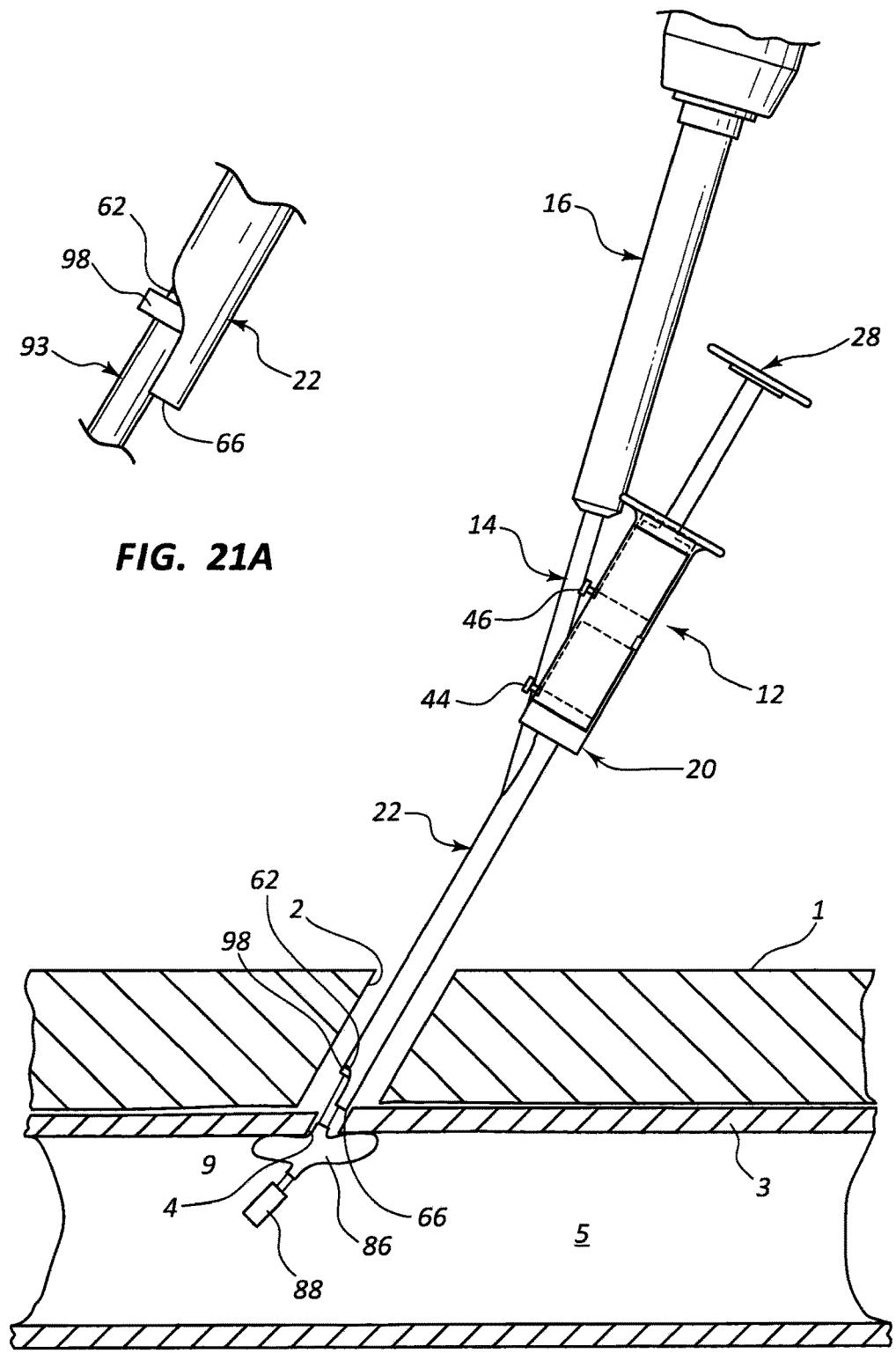

Referring now to FIGS. 20-23, an example method of treating a tissue puncture using a vascular closure system having the sealant delivery device 12 is shown and described. FIG. 20 shows balloon inflation device 14 and sheath 16 being advanced through a tissue tract 2 of a tissue layer 1 and through a vessel puncture 4 to a vessel interior 5. In some arrangements, at least one suture is positioned extending through a wall of vessel 3 prior to advancing balloon inflation device 14 and sheath 16 through the vessel puncture 4. The balloon 86 is then inflated via the inflation source 84 and drawn into contact with an inner surface of vessel 3 adjacent to vessel puncture 4 (see FIG. 21). The inflated balloon 86 provides a temporary seal of the vessel puncture 4 and may also act as an anchor and reference point for operation of other functions of vascular closure system 10.

Sheath 16 may be withdrawn proximately along balloon inflation device 14 so that the sealant delivery device 12 can be inserted through the tissue tract 2. In at least one example, the sealant delivery device 12 is mounted to the balloon inflation device 14 at the exchange port 96. The sealant delivery device 12 may be advanced distally along the balloon inflation device 14 to position the distal end 54 adjacent to tissue puncture 4. A collar 98 may act as a position stop to position distal end 54 at a location spaced proximal of the vessel puncture 4 so that the sealant delivered by sealant delivery device 12 may flow more freely into tissue tract 2 and vessel puncture 4.

Figure 22:
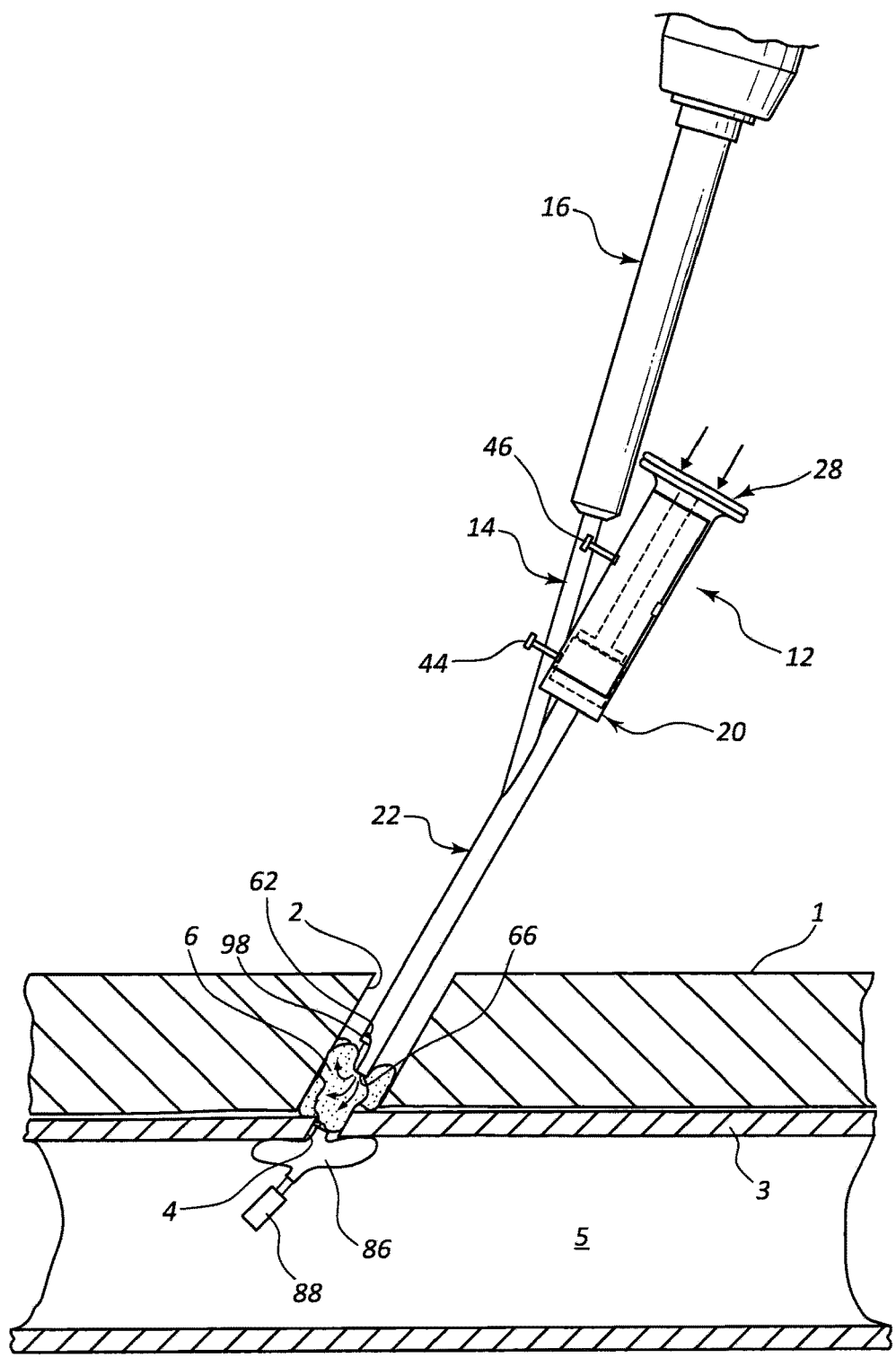
Figure 23:
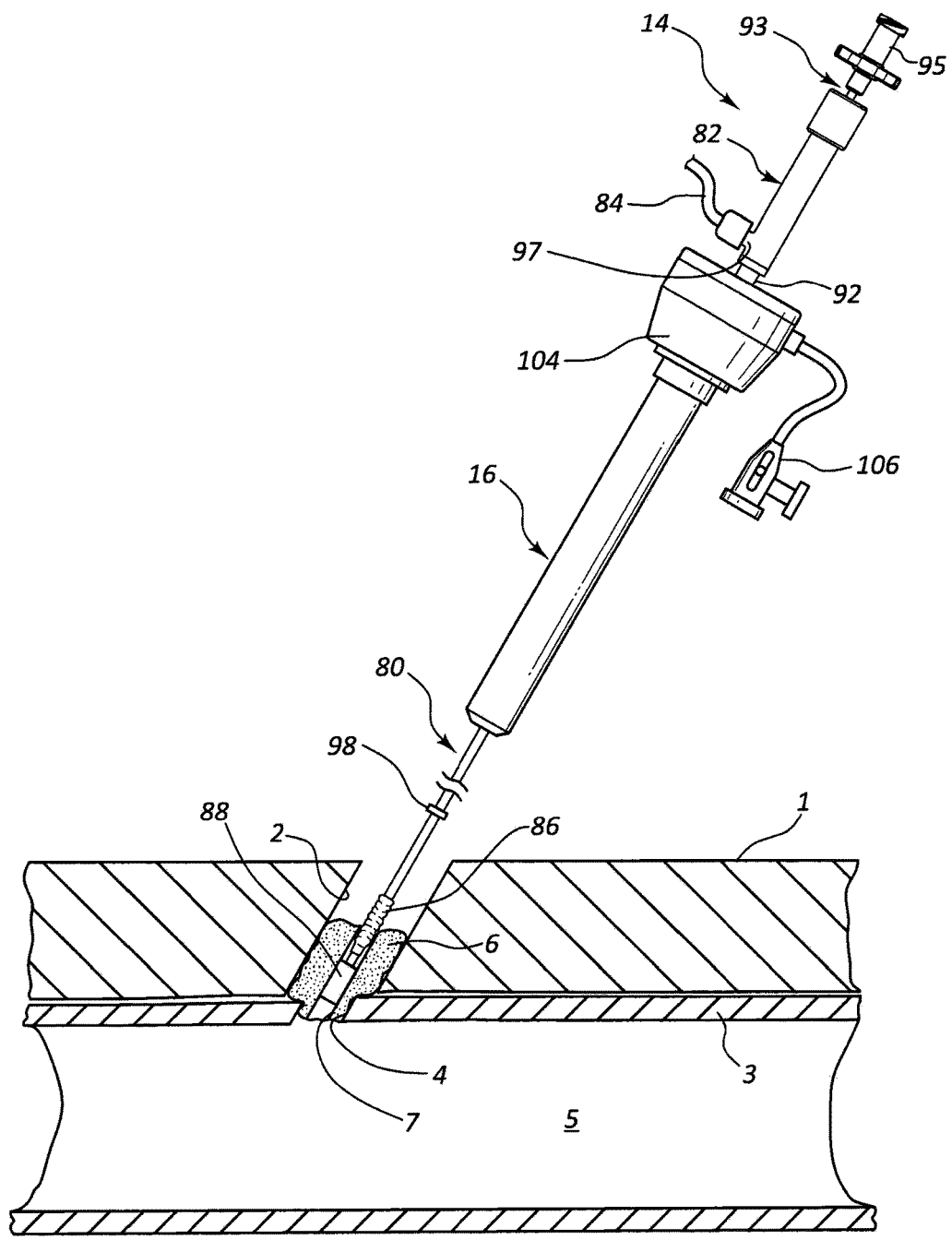

Referring to FIG. 22, the plunger assembly 26 is operated to advance the sealant carried by cartridge 24 through delivery tube 222 and out of distal end 54 to fill the tissue tract 2 and vessel puncture 4. The sealant may form a sealant plug 6 (see FIG. 23).

The sealant delivery device 12 may be withdrawn, the balloon 86 deflated, and the balloon inflation device 14 withdrawn to position the detachable tip 88 within a plug channel 7 formed in sealant plug 6. The detachable tip 88 may be detached and lodged within sealant plug 6 to further seal vessel puncture 4 and tissue tract 2. In some arrangements, a secondary volume of sealant may be deposited in tissue tract 2 proximal of sealant plug 6. The secondary sealant may be delivered via the balloon inflation device 14 (e.g., via the inner tube 93) or using the sealant delivery device 12.

Referring now to FIGS. 24-24A, another example sealant delivery device 412 is shown. Sealant delivery device 412 includes some of the features of sealant delivery device 12 and features of balloon inflation device 14 (see FIG. 19). Sealant delivery device 412 may include a housing 420 having distal and proximal ends 430, 432, a delivery tube 422, first and second sealant containers 424, 426, and a plunger assembly 428. The sealant delivery device 412 may also include a balloon location device 482, a balloon 486 and an inner tube 493. The inner tube 493 may extend through the delivery tube 422. The balloon 486 may be connected to at least one of the delivery tube 422 and the inner tube 493.

The housing 420 may include a mixing chamber 438. Delivery tube 422 may include distal and proximal ends 454, 456 and first and second lumens 458, 460, which include distal openings 462, 466, respectively. The first and second sealant containers 424, 426 hold first and second sealant components. Operating the plunger assembly 428 ejects sealant components held by the first and second sealant containers 424, 426 through the first lumen 458 to be ejected at the distal opening 462 to help seal a vessel puncture.

Many types of handle assembly and cartridge designs may be used with sealant delivery device 412. Sealant delivery device 412 may be configured to hold multiple sealant containers. The sealant containers may be provided separate from the housing 420 and moved into and out of the housing either laterally or longitudinally.

The use of sealant containers that each carries a sealant component may have advantages over other types of sealant delivery devices. Such sealant containers may be quickly interchanged to provide the operator with a desired combination of sealant components for a particular procedure. The sealant containers may be mounted within the housing of the sealant delivery device during manufacture and assembly of the sealant delivery device prior to shipping and storage and later use of the sealant delivery device by an operator. Alternatively, the operator may insert the sealant containers into the housing of the sealant delivery device just before use by the operator. The sealant delivery device may include features (e.g., first and second sliders 444, 446) that help hold the sealant containers within the housing in positions spaced apart from features that would create flow communication between the sealant containers. These features may be operated to permit creation of the flow communication between containers just before or during use of the sealant delivery device.

The sealants discussed herein may comprise different sealant materials such as bioadhesives. The sealants may include a single component, or may comprise multiple sealant components that are mixed together. The sealant components may be naturally derived or synthetic. The sealant components may be cross-linked. Some example synthetic components include polyethers such as polyethylene glycol, polypropylene glycol and polytetrahydrofuran. Other synthetic components may include polyamine compositions such as polyvinylpyrrolidones and polyethylene imines. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may be cross-linked by any known method including, for example, condensation reactions, Michael addition, and free radical. Functional groups used for cross-linking may include, for example, thiols, acrylates, amines, succinimydyls and aldehydes.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A closure device operable to seal a vessel puncture, comprising:
   a delivery member insertable through a tissue tract to the vessel puncture;
   a sealant material applicator configured to supply a volume of sealant material to the delivery member, the sealant material applicator comprising:
   a housing having at least first and second chambers, the delivery member being in fluid communication with the first and second chambers, the first chamber carrying a first sealant component of the sealant material and the second chamber carrying a second sealant component of the sealant material;
   a plunger assembly having at least first and second plunger members insertable into the first and second chambers, respectively;
   at least one container positioned in the first or second chamber, the at least one container carrying a third sealant component of the sealant material;
   wherein the sealant material applicator is operable to create flow communication between the at least one container and at least one of the first and second chambers to mix the third sealant component with at least one of the first and second sealant components prior to creating the volume of sealant material.

2. The closure device of claim 1, wherein the sealant material applicator is operable to deliver the volume of sealant material through the delivery member and to the tissue tract to seal the vessel puncture from outside the vessel.

3. The closure device of claim 1, wherein the sealant material applicator includes a mixing chamber at a distal end thereof, the first, second and third sealant components being at least partially mixed in the mixing chamber before being ejected from the sealant material applicator as the sealant material.

4. The closure device of claim 1, wherein the at least one container is positioned within the first chamber and exposed to the first sealant component, and operating the sealant material applicator ruptures the at least one container to create flow communication between the at least one container and the first chamber.

5. The closure device of claim 1, wherein the first sealant component is carried in a first container, the first container being positioned in the first chamber, the second sealant component is carried in a second container, the second container being positioned in the second chamber, and the at least one container comprises a third container carrying the third sealant component, the third container being positioned in the first or second chamber.

6. The closure device of claim 5, wherein operating plunger assembly creates flow communication between the third container and the first container to combine the first and third sealant components prior to ejecting the volume of sealant material to the delivery member.

7. The closure device of claim 5, wherein the first, second and third sealant components are mixed within a mixing chamber of the sealant material applicator prior to being ejected from the sealant material applicator.

8. The closure device of claim 5, wherein the sealant material applicator includes at least one needle configured to create the flow communication.

9. The closure device of claim 5, wherein at least one of the first, second and third containers includes a frangible seal.

* * * * *